(12) United States Patent
de Naray et al.

(10) Patent No.: US 11,294,110 B2
(45) Date of Patent: Apr. 5, 2022

(54) FABRICATING DIFFRACTIVE STRUCTURES ON GEMSTONES FOR HIGH OPTICAL PERFORMANCE

(71) Applicant: Sparkle Cut Diamonds, Inc., St. Augustine, FL (US)

(72) Inventors: Mark L. de Naray, St. Augustine, FL (US); Kurt Philip Schoeckert, Hartford, WI (US); Lance Richardson, Ponte Vedra, FL (US)

(73) Assignee: SPARKLE CUT DIAMONDS, INC., St. Augustine, FL (US)

( * ) Notice: Subject to any disclaimer, the term of this patent is extended or adjusted under 35 U.S.C. 154(b) by 192 days.

(21) Appl. No.: 16/503,120

(22) Filed: Jul. 3, 2019

(65) Prior Publication Data

US 2020/0121040 A1   Apr. 23, 2020

Related U.S. Application Data

(60) Provisional application No. 62/749,603, filed on Oct. 23, 2018.

(51) Int. Cl.
*A44C 17/00* (2006.01)
*A44C 27/00* (2006.01)
*C23C 30/00* (2006.01)
*H01J 37/31* (2006.01)
*G02B 5/18* (2006.01)
(Continued)

(52) U.S. Cl.
CPC .......... *G02B 5/1857* (2013.01); *A44C 17/001* (2013.01); *A44C 27/006* (2013.01); *B23K 15/00* (2013.01); *B23K 15/0033* (2013.01); *B23K 15/08* (2013.01); *B44C 1/228* (2013.01); *C30B 33/04* (2013.01); *G01N 21/87* (2013.01);
(Continued)

(58) Field of Classification Search
None
See application file for complete search history.

(56) References Cited

U.S. PATENT DOCUMENTS 3,808,836 A * 5/1974 Jones .................. A44C 17/003
63/32
6,187,213 B1   2/2001 Smith et al.
(Continued)

FOREIGN PATENT DOCUMENTS

WO   WO 2018/067022   4/2018

OTHER PUBLICATIONS

U.S. Appl. No. 62/540,844, filed Aug. 3, 2017, Maltezos et al.
(Continued)

*Primary Examiner* — Ashok Patel
(74) *Attorney, Agent, or Firm* — Minta Law Group LC; Veronica-Adele R. Cao

(57) ABSTRACT

Methods, apparatus, and systems for fabricating diffractive structures on gemstones for high optical performance are provided. In one aspect, a method includes obtaining a plurality of gemstone characteristics of a gemstone, determining that the gemstone exhibits each of the plurality of gemstone characteristics within a respective predetermined range, identifying a diffractive structure setting associated with a combination of the respective predetermined ranges for the plurality of gemstone characteristics, and fabricating diffractive structures on the gemstone according to the diffractive structure setting.

19 Claims, 10 Drawing Sheets

(51) Int. Cl.
| | |
|---|---|
| *G01N 21/87* | (2006.01) |
| *B23K 15/00* | (2006.01) |
| *C30B 33/04* | (2006.01) |
| *G16C 60/00* | (2019.01) |
| *B44C 1/22* | (2006.01) |
| *B23K 15/08* | (2006.01) |
| *G01N 33/38* | (2006.01) |

(52) U.S. Cl.
 CPC .............. *G16C 60/00* (2019.02); *C23C 30/00* (2013.01); *G01N 33/381* (2013.01); *H01J 37/31* (2013.01)

(56) References Cited

U.S. PATENT DOCUMENTS

| | | | |
|---|---|---|---|
| 8,233,218 B1 | 7/2012 | Mossberg et al. | |
| 8,479,538 B2 | 7/2013 | Maltezos et al. | |
| 2007/0157667 A1* | 7/2007 | Maltezos | ............... A44C 17/00 63/32 |
| 2014/0075991 A1 | 3/2014 | He | |
| 2014/0107986 A1 | 4/2014 | Sivovolenko | |
| 2015/0101365 A1 | 4/2015 | Hui et al. | |
| 2019/0037980 A1 | 2/2019 | Maltezos et al. | |

OTHER PUBLICATIONS

[online] Smutny, "Light propagation in transparent polyhedral," Retrieved from the Internet on Nov. 25, 2016: URL:ftp://cmp.felk.cvut.cz/pub/cmp/articles/smutny/Smutny-TR-2014-11.pdf dated Aug. 31, 2014, 135 pages.

Babinec et al., "Design and focused ion beam fabrication of single crystal diamond nanobeam cavities," Journal of Vacuum Science & Technology B, Nanotechnology and Microelectronics: Materials, Processing, Measurement, and Phenomena 29(1):010601, Jan. 10, 2011.

International Search Report and Written Opinion in Application No. PCT/US2018/045020, dated Jan. 16, 2019, 18 pages.

Vargas Catalan, "Microfabrication of Optical Components in Synthetic Diamond: Infrared Optics for Applications in Astronomy and Spectroscopy," Doctoral Dissertation, Acta Universitatis Upsaliensis, 2018, 1 page.

Xu et al., "Fabrication of micro DOE using micro tools shaped with focused ion beam." Optics express 18(8):8025-8032, Apr. 12, 2010.

Zinoviev et al., "Diffraction grating couplers milled in Si 3 N 4 rib waveguides with a focused ion beam." Optics express 13(21):8618-8624. Oct. 17, 2005.

International Preliminary Report on Patentability in Application No. PCT/US2018/045020, dated Feb. 4, 2020, 11 pages.

* cited by examiner

| Diffractive Structure Setting | Ranges of Gemstone Characteristics (C) |
|---|---|
| 1 | R11 for C1, R12 for C2, … |
| 2 | R21 for C1, R22 for C2, … |
| ⋯ | ⋯ |
| n | Rn1 for C1, Rn2 for C2, … |

FIG. 4

FABRICATING DIFFRACTIVE STRUCTURES ON GEMSTONES FOR HIGH OPTICAL PERFORMANCE

CROSS-REFERENCE TO RELATED APPLICATION

This application claims priority under 35 USC § 119(e) to U.S. Provisional Patent Application Ser. No. 62/749,603, filed on Oct. 23, 2018, the entire content of which is hereby incorporated by reference.

TECHNICAL FIELD

This disclosure relates to gemstones and jewelry, and more particularly to fabricating diffractive structures on gemstones or jewelry for high optical performance.

BACKGROUND

Gemstones are prized for their rarity and beauty. Among gemstones, particularly diamonds, are highly valued. When used for their aesthetic quality, diamond crystals are often cut and polished in ways that emphasize certain optical properties, e.g., scintillation, brilliance, or fire. Some methods have been developed to put diffraction gratings on diamonds to enhance their optical properties such as sparkle and fire. However, as the diamonds are generally handmade, e.g., from natural stones, and can have vastly different optical qualities, it is difficult for the methods to be consistent on light performance improvement. Furthermore, it is costly to use the methods to manufacture the diffraction gratings on the diamonds.

SUMMARY

The present disclosure describes methods, apparatus, and systems for fabricating diffractive structures (e.g., diffraction gratings) on surfaces of gemstones (e.g., diamonds) for high optical performance (e.g., brilliance, fire, and/or scintillation) of the gemstones. Particularly, implementations of the present disclosure can achieve highly repetitive and high-volume manufacturing gemstones having predictable, reliable and increased optical performance with reduced complexity, time and cost. Implementations of the present disclosure can also reduce visibility of grating marks on diamonds' facets, improve light performance and reduce complexity, time, and cost for locating high optical value regions on diamond facets to have diffractive structures applied on to improve light performance.

One aspect of the present disclosure features a method including: obtaining a plurality of gemstone characteristics of a first gemstone, determining that the first gemstone exhibits each of the plurality of gemstone characteristics within a respective first predetermined range, and identifying, for the first gemstone, a first diffractive structure setting associated with a first combination of the respective first predetermined ranges for the plurality of gemstone characteristics.

The method can further include fabricating first diffractive structures on the first gemstone according to the first diffractive structure setting. In some cases, the method includes determining that each of a plurality of first gemstones exhibits the plurality of gemstone characteristics within the respective first predetermined ranges and fabricating respective diffractive structures in each of the plurality of first gemstones according to the first diffractive structure setting.

In some cases, fabricating the diffractive structure on the gemstone includes: milling the diffractive structures on the facets of the gemstone by using a focused ion beam and removing ion material residue in the fabricated diffractive structures. Removing the ion material residue in the fabricated diffractive structures can include: heating the gemstone with the fabricated diffractive structures in a container to reduce an amount of the ion material residue in the gemstone. Before the heating, the container can be purged with inert gas to reduce an amount of oxygen in the container. In some examples, the container is an oven and is heated to a temperature between 1100-1200 degrees Fahrenheit and the ion material residue is melted at the temperature. The container can heated at a temperature for a time period determined based on one or more characteristics of the gemstone including a weight. In some cases, before the milling, a metallic coating can be deposited on the gemstone. A thickness of the metallic coating can be controlled such that the metallic coating is thick enough to dissipate charges caused by the focused ion beam and is thin enough for the focused ion beam to go through. The metallic coating can include one of gold and gold palladium.

In some cases, the method includes determining that each of a plurality of second gemstones exhibits each of the plurality of gemstone characteristics within a respective second predetermined range and identifying a second diffractive structure setting associated with a second combination of the respective second predetermined ranges for the plurality of gemstone characteristics, the second combination being different from the first combination and the second diffractive setting being different from the first diffractive setting. The method can further include fabricating respective diffractive structures on each of the plurality of second gemstones according to the second diffractive structure setting.

The first diffractive structure setting and the first combination can be stored and associated in a repository that stores and associates respective diffractive structure settings with different combinations of ranges of gemstone characteristics.

The plurality of gemstone characteristics can include at least a first gemstone characteristic and a second gemstone characteristic. Determining that the first gemstone exhibits each of the plurality of gemstone characteristics within a respective first predetermined range can include determining that the first gemstone exhibits the first gemstone characteristic within a first predetermined range and a second gemstone characteristic within a second predetermined range.

The first gemstone can be a diamond having a culet, a pavilion, a girdle, a crown, and a table, and the plurality of gemstone characteristics can include one or more of a crown percentage, a table percentage, a depth proportion, a joint angle between a crown and a pavilion, and symmetry.

The first diffractive structure setting can include information of a plurality of facets of a gemstone to be fabricated with diffractive structures, information of a respective high-optical-value (HOV) region on each of the plurality of facets, and information of a respective diffractive structure to be fabricated in the respective HOV region on each of the plurality of facets. The plurality of facets can be selected from a total number of facets of the gemstone, and a number of the plurality of facets can be smaller than the total number of facets of the gemstone.

In some cases, the selected facets are not opposite to each other. In some examples, the total number of facets of the gemstone is 8, and the number of the plurality of selected facets is no more than 4. In a particular example, the gemstone comprises first, second, third, fourth, fifth, sixth, seventh, and eighth sequential facets, and the selected facets include: first, second, third and fourth facets, first, second, third, and eighth facets, first, second, fourth, and seventh facets, first, third, fourth and sixth facets, or first, third, sixth, and eighth facets.

The information of the respective diffractive structure can include one or more of parameters of the respective diffractive structure including a depth, a pitch, uniformity, a shape, an angle, and a number of cuts. The information of the respective high-optical-value (HOV) region on each of the plurality of facets can include: a relative location of the respective HOV region on the facet, a shape of the respective HOV region, and a relative size of the respective HOV region to the facet.

The method can further include determining a corresponding diffractive structure setting for the first gemstone based on the first diffractive structure setting and geometry information of the first gemstone and fabricating corresponding diffractive structures on respective HOV regions of selected facets of the first gemstone according to the corresponding diffractive structure setting for the first gemstone.

The plurality of gemstone characteristics of the first gemstone can be obtained based on geometrical cut parameters of the first gemstone. The plurality of gemstone characteristics of the first gemstone can be obtained based on a three-dimensional model of the first gemstone. The plurality of gemstone characteristics of the first gemstone can be also obtained based on geometrical measurement of an outer surface of the first gemstone.

Another aspect of the present disclosure features a gemstone including an outer surface having a plurality of facets and diffractive structures fabricated on one or more facets of the plurality of facets. The one or more facets fabricated with the diffractive structures are not opposite to each other.

In some examples, the outer surface comprises first, second, third, fourth, fifth, sixth, seventh, and eighth facets in sequence, and the facets fabricated with the diffractive structures include: first, second, third and fourth facets, first, second, third, and eighth facets, first, second, fourth, and seventh facets, first, third, fourth and sixth facets, or first, third, sixth, and eighth facets.

The gemstone can be a round cut diamond, and the plurality of facets can include eight pavilion lower main facets, and a number of the facets fabricated with the diffractive structures can be no more than 4.

A third aspect of the present disclosure features a method including fabricating diffractive structures on one or more facets of a gemstone, the facets being not opposite to each other and cleaning the fabricated diffractive structures.

In some implementations, fabricating the diffractive structures includes milling the diffractive structures on the facets of the gemstone by using a focused ion beam. Cleaning the fabricated diffractive structures can include removing ion material remaining in the fabricated diffractive structures.

In some implementations, fabricating the diffractive structures includes plasma etching the diffractive structures on the facets of the gemstone.

A fourth aspect of the present disclosure features a method including providing a metallic coating on a gemstone and fabricating a diffractive structure on the gemstone via a focused ion beam. The metallic coating is configured to dissipate charges caused by the focused ion beam.

A thickness of the metallic coating can be controlled such that the metallic coating is thick enough to dissipate the charges caused by the focused ion beam and is thin enough for the focused ion beam to go through.

In some examples, the metallic coating includes gold. In some examples, the metallic coating includes gold palladium.

The focused ion beam can be from a gallium ion source, and the focused ion beam can include Ga+ ions.

The diffractive structure can be fabricated on a region of a surface of the gemstone, and ion material of the focused ion beam is impregnated in the region during the fabrication and remains on the diffractive structure after the fabrication. The method can further include removing the ion material remaining in the diffractive structure.

A fifth aspect of the present disclosure features positioning a gemstone with ion material residue in a container and heating the container to clean the ion material residue so as to reduce an amount of the ion material residue in the gemstone.

Before the heating, the method can further include reducing an amount of oxygen in the container. The amount of oxygen in the container can be reduced by purging the container with inert gas. Reducing an amount of oxygen in the container can include removing substantially all of the oxygen in the container.

In some cases, the container is an oven and is heated to a temperature between 1100-1200 degrees Fahrenheit and the ion material residue is melted at the temperature. The container is heated no higher than 1300 degrees Fahrenheit while the gemstone is positioned in the container.

In some cases, heating the container to clean the ion material residue can include heating the container at a temperature for a time period (or a dwell time) determined based on one or more characteristics of the gemstone. The one or more characteristics of the gemstone can include a weight of the gemstone.

In some cases, the ion material residue includes gallium. In some cases, cleaning the ion material residue removes substantially all of the ion material residue visible at a 30× magnification.

A sixth aspect of the present disclosure features a method including obtaining a plurality of gemstone characteristics of a gemstone, determining that the gemstone exhibits each of the plurality of gemstone characteristics within a respective predetermined range; identifying, in a repository, a diffractive structure setting associated with a combination of the respective predetermined ranges for the plurality of gemstone characteristics, the repository being configured to store and associate respective diffractive structure settings with different combinations of ranges of gemstone characteristics; determining a corresponding diffractive structure setting for the gemstone based on the identified diffractive structure setting and geometry information of the gemstone, wherein the corresponding diffractive structure setting comprises information of a plurality of facets selected to be fabricated with diffractive structures, information of a respective high-optical-value (HOV) region on each of the selected facets, and information of a respective diffractive structure to be fabricated in the respective HOV region on each of the selected facets; and fabricating the respective diffractive structures on the respective HOV regions of the selected facets of the gemstone according to the determined corresponding diffractive structure setting.

Fabricating the respective diffractive structures on the respective HOV regions of the selected facets of the gemstone can include: depositing a metallic coating on the selected facets; and fabricating the diffractive structures on the respective HOV regions of the selected facets via a focused ion beam, where the metallic coating is configured to dissipate charges caused by the focused ion beam.

Ion material of the focused ion beam can be impregnated in the HOV regions during the fabrication and remains on the diffractive structures after the fabrication. The method can further include: after the fabrication, positioning the gemstone with the remaining ion material in a container; purging the container with inert gas to remove substantially all of oxygen in the container; and heating the container to a temperature within a predetermined range to melt the remaining ion material so as to remove substantially all of the remaining ion material visible at a 30× magnification.

A seventh aspect of the present disclosure features a method including: identifying a plurality of gemstone characteristics comprising at least a first gemstone characteristic and a second gemstone characteristic; fabricating diffractive structures in a first plurality of gemstones according to a first diffractive structure plan, where the first plurality of gemstones each exhibit the first gemstone characteristic within a first range and exhibit the second gemstone characteristic within a second range; and fabricating diffractive structures in a second plurality of gemstones according to a second diffractive structure plan that is different than the first diffractive structure plan, wherein the second plurality of gemstones each exhibit the first gemstone characteristic within a third range that is different than the first range and exhibit the second gemstone characteristic within a fourth range that is different than the second range.

An eighth aspect of the present disclosure features a method of improving optical performance of gemstones with diffractive structures. The method includes: determining a first region on a first surface of a first gemstone based on information of a high optical value region on a corresponding surface of a representative gemstone and fabricating a first diffractive structure on the first region on the first surface of the first gemstone. The first gemstone has a geometry similar to a geometry of the representative gemstone. The high optical value region on the corresponding surface of the representative gemstone corresponds to a particular region on the first surface of the first gemstone, and the first region can include the particular region.

The method can further include: measuring first optical performance of the first gemstone with the fabricated first diffractive structure; determining a second region on the first surface of the first gemstone based on the measured first optical performance, where the second region is within the first region and includes the particular region; and fabricating a second diffractive structure on the second region on the first surface of the first gemstone. The second diffractive structure has a property substantially the same as that of the first diffractive structure.

The method can include measuring second optical performance of the first gemstone with the fabricated second diffractive structure. In some cases, a third region on the first surface of the first gemstone can be determined based on the measured second optical performance. The third region can be within the second region and includes the particular region. In some cases, a third region on the first surface of the first gemstone can be determined based on the measured first optical performance and second optical performance, where the third region includes the particular region.

In some cases, determining the third region can include: determining that the second optical performance is higher than the first optical performance; and determining the third region to be within the second region. In some cases, determining the third region includes: determining that the first optical performance is higher than the second optical performance; and determining the third region to be within the first region and larger than the second region.

The method can further include: fabricating a third diffractive structure on the third region on the first surface of the first gemstone; and measuring third optical performance of the first gemstone with the fabricated third diffractive structure. The third diffractive structure has a property substantially same as that of the second diffractive structure.

In some cases, the method includes: determining that the third optical performance is substantially the same as the second optical performance, and in response, determining that the third region is a target region without further optimization. In some cases, the method includes: determining that the third optical performance is substantially same as a predetermined optical performance, and in response, determining that the third region is a target region without further optimization. The third optical performance can be more than 50% higher than an optical performance of the gemstone without the third diffractive structure. Particularly, the third optical performance can be more than 75% higher than the optical performance of the gemstone without the third diffractive structure. The third optical performance can include scintillation.

In some examples, the predetermined optical performance is determined based on a particular optical performance of the representative gemstone with a particular diffractive structure arranged on the high optical value region on the corresponding surface of the representative gemstone. The third diffractive structure can have a property substantially same as that of the particular diffractive structure.

The first optical performance can include at least one of brilliance, fire, or scintillation. The first diffractive structure can include a diffraction grating having a property defined by one or more parameters including a period, a depth, a width, an orientation, a shape, and a blaze angle. An edge of the first region defines a boundary of the first diffractive structure.

In some implementations, the method includes obtaining a three-dimensional model of the representative gemstone; and identifying the high optical value region on the corresponding surface of the representative gemstone by analyzing the three-dimensional model of the representative gemstone, the high optical value region having an optical value higher than one or more other regions on the corresponding surface of the representative gemstone.

The method can further include: determining a particular diffractive structure to be arranged on the identified high optical value region of the corresponding surface of the representative gemstone, such that the representative gemstone with the particular diffractive structure has a higher optical performance than the representative gemstone without the particular diffractive structure. The first diffractive structure can have a property substantially the same as that of the particular diffractive structure.

In some implementations, analyzing the three-dimensional model of the representative gemstone includes: simulating propagation of an incident light through the representative gemstone and reflected by the corresponding surface; and generating irradiance data representing light reflection distribution of the light on the representative surface. Identifying the high optical value region on the corresponding surface of the representative gemstone can include: determining the high optical value region based on the generated irradiance data representing the light reflection distribution on the corresponding surface, where the optical value is defined as a ratio of an energy enclosed in the high optical value region and a total energy enclosed in the corresponding surface in the irradiance data.

The first region on the first surface of the first gemstone can be determined without obtaining a three-dimensional model of the first gemstone.

In some implementations, the method includes: determining a second region on a second surface of the first gemstone based on information of a second high optical value region on a second corresponding surface of the representative gemstone, where the second high optical value region on the corresponding surface of the representative gemstone corresponds to a second particular region on the second surface of the first gemstone, and the second region includes the second particular region; and fabricating a second diffractive structure on the second region on the second surface of the first gemstone.

In some implementations, the method includes: determining a second region on a second surface of a second gemstone based on information of the high optical value region on the corresponding surface of the representative gemstone, where the second gemstone has a geometry similar to the geometry of the representative gemstone, and where the high optical value region on the corresponding surface of the representative gemstone corresponds to a second particular region on the second surface of the second gemstone, and the second region includes the second particular region; and fabricating a second diffractive structure on the second region on the second surface of the second gemstone.

The first region can encompass the particular region and have a size larger than the particular region. The size of the first region can be larger than the size of the particular region by a particular percent, and the particular percent can be larger than 5%, 10%, 15%, or 20%. The first region can extend from the particular region along a vertical axis of the first surface and/or a horizontal axis of the first surface.

In some examples, the first gemstone is a diamond having a culet, pavilions, a girdle, a crown, and a table, and the first surface is a pavilion lower main facet extending along a direction from the culet to the girdle, and the geometry of the first gemstone includes a height of the facet, a diameter of the diamond, and a depth of the diamond.

The method can include: receiving information of the geometry of the first gemstone; and selecting the representative gemstone from a database based on the information of the geometry of the first gemstone and the geometry of the representative gemstone, where the database includes information of multiple representative gemstones that have different geometries.

A ninth aspect of the present disclosure features a method of improving optical performance of gemstones with diffractive structures, including: determining a high optical value region on a surface of a gemstone; and controlling fabrication of a diffractive structure on the high optical value region on the surface of the gemstone, such that the optical performance of the gemstone with the diffractive structure is improved.

For example, the diffractive structure on the gemstone can have little visibility or be invisible to the human eye with a jeweler's loupe. The loupe can have a magnification of no less than 5×, 10×, 15×, 20×, 25×, or 30×.

In some implementations, controlling fabrication of the diffractive structure includes: controlling the fabrication to reach a predetermined value of at least one of parameters of the diffractive structure, the parameters including a depth, a pitch, uniformity, a shape, an angle, an orientation, and a number of cuts.

In some implementations, controlling fabrication of the diffractive structure includes: controlling a fabrication process of the diffractive structure. Controlling the fabrication process of the diffractive structure can include: fabricating the diffractive structure by focusing a beam of ions from an ion source (e.g., a gallium ion source) on the high optical value region on the surface of the gemstone, where the ion material (e.g., gallium) is impregnated in the high optical value region and remaining on the diffractive structure to make the diffractive structure visible; and removing the ion material (e.g., gallium) remaining in the diffractive structure (or on a surface of the diffractive structure). The ions can include Ga+ ions.

In some examples, removing the ion material (e.g., gallium) remaining on the diffractive structure includes: heating the diffractive structure to melt (and/or evaporate) the ion materials to clean the ion material from the diffractive structure.

A tenth aspect of the present disclosure features a method of improving optical performance of gemstones with diffractive structures, including: fabricating a diffractive structure on a particular region on a surface of a gemstone by using a focused ion beam; and removing ion material (remaining in the diffractive structure. The particular region includes a high optical value region.

The ion material can be impregnated in the particular region during the fabrication and ion material can remain in the diffractive structure (or on the surface of the diffractive structure) to make the diffractive structure visible. The focused ion beam can be from a gallium ion source, the ions can include Ga+ ions, and the ion material that remains in the diffractive structure can be gallium or a composite of gallium and one or more elements in an environment of a chamber or diamond, e.g., oxygen or Xenon. In one example, the ion material is oxidized gallium. Removing the ion material remaining in the diffractive structure can include: heating the diffractive structure to melt the ion material.

After removing the ion material residue on the diffractive structure, the diffractive structure on the gemstone can have little visibility or be invisible to the human eye without or with a jeweler's loupe. The loupe can be a magnification of no less than 5×, 10×, 15×, 20×, 25×, or 30×.

An eleventh aspect of the present disclosure features a method of improving optical performance of gemstones with diffractive structures. The method includes: determining an initial region on a surface of a gemstone based on information of a high optical value region on a corresponding surface of a representative gemstone, where the gemstone has a geometry similar to a geometry of the representative gemstone, and where the high optical value region on the corresponding surface of the representative gemstone corresponds to a particular region on the surface of the gemstone, and the initial region includes the particular region; fabricating a diffractive structure on the initial region on the surface of the gemstone; measuring an initial optical performance of the gemstone with the diffractive structure on the initial region of the surface of the gemstone; determining a second region based on the initial optical performance, the second region being within the initial region and including the particular region; fabricating a second diffractive structure on the second region; measuring a second optical performance of the gemstone with the second diffractive structure on the second region of the surface of the gemstone; and, in response to determining that the second optical performance is higher than the original optical performance, continuing determining a third region in the second region.

The method can further include: fabricating a third diffractive structure on the third region on the surface; and measuring a third optical performance of the gemstone with the third diffractive structure.

In some cases, the method further includes: determining that the third optical performance is substantially identical to the second optical performance, and in response, determining that the third region is a high optical value region on the surface of the gemstone. In some cases, the method further includes: determining that the third optical performance is higher than the second optical performance, and in response, continuing determining a fourth region in the third region. In some cases, the method further includes: determining that the third optical performance is smaller than the second optical performance, and in response, continuing determining a fourth region in the second region, the fourth region being larger than the third region.

The gemstone can be a diamond having a culet, a pavilion, a girdle, a crown, and a table, and the first surface can be a pavilion lower main facet extending along a direction from the culet to the girdle. Along the direction, the third region can have a smaller size than the second region that can have a smaller size than the initial region.

A twelfth aspect of the present disclosure features a method including: testing at least first, second, and third gemstones to determine a composite diffractive structure; and applying the composite diffractive structure to each of fourth, fifth, and sixth gemstones that each have shape that is at least partially different from that of each of the first, second, and third gemstones.

The composite diffractive structure can be applied to the fourth, fifth, and sixth gemstones without obtaining a three-dimensional model of any of the fourth, fifth, and sixth gemstones. The composite diffractive structure can be applied to the fourth, fifth, and sixth gemstones prior to obtaining a three-dimensional model of any of the fourth, fifth, and sixth gemstones. The composite diffractive structure can be suitable for diffracting light when applied to each of the fourth, fifth, and sixth gemstones and be not ideal for diffracting light when applied to any of the fourth, fifth, and sixth gemstones. The composite diffractive structure can include an identified grating pitch, an identified grating depth, an identified grating spacing, and an identified grating design.

A thirteenth aspect of the present disclosure features a method including: patterning a first diffractive structure to a first gemstone that is a function of a first facet height of the first gemstone and a first table diameter of the first gemstone without modeling the first gemstone; patterning a second diffractive structure to a second gemstone that is a function of a second facet height of the second gemstone and a second table diameter of the second gemstone without modeling the second gemstone; and patterning a third diffractive structure to a third gemstone that is a function of a third facet height of the third gemstone and a third table diameter of the third gemstone without modeling the third gemstone. The first diffractive structure is different than the second diffractive structure, the second diffractive structure is different than the third diffractive structure, and the third diffractive structure is different than the first diffractive structure. The composite diffractive structure can include an identified grating pitch, an identified grating depth, an identified grating spacing, and an identified grating design.

A fourteenth aspect of the present disclosure features a method including: fabricating a diffractive structure into a gemstone via a focused ion beam; and after the diffractive structure is patterned on the gemstone via the focused ion beam, removing ion material from the diffractive structure of the gemstone. Fabricating the diffractive structure can include milling the diffractive structure via the focused ion beam. The focused ion beam can be a gallium element focused ion beam or any other suitable type of ion beam. For example, fabricating can use a gallium focused ion beam element, an oxygen focused ion beam element, a xenon focused ion beam element, or another suitable focused ion beam element that is suitable for the application.

A fifteenth aspect of the present disclosure features a method including: obtaining, by one or more processors, a first three-dimensional model of a first gemstone including representations of surfaces of the first gemstone; identifying, by the one or more processors, a first region on a first surface of the first gemstone having a first optical value higher than one or more other regions on the first surface of the first gemstone by analyzing the first three-dimensional model of the first gemstone; determining, by the one or more processors, a first diffractive structure to be arranged on the identified first region of the first surface of the first gemstone, such that the first gemstone with the first diffractive structure has a first higher optical performance than the first gemstone without the first diffractive structure; obtaining, by the one or more processors, a second three-dimensional model of a second gemstone including representations of surfaces of the second gemstone; identifying, by the one or more processors, a second region on a second surface of the second gemstone having a second optical value higher than one or more other regions on the second surface of the second gemstone by analyzing the second three-dimensional model of the second gemstone; determining, by the one or more processors, a second diffractive structure to be arranged on the identified second region of the second surface of the second gemstone, such that the second gemstone with the second diffractive structure has a second higher optical performance than the second gemstone without the second diffractive structure; obtaining, by the one or more processors, a third three-dimensional model of a third gemstone including representations of surfaces of the third gemstone; identifying, by the one or more processors, a third region on a third surface of the third gemstone having a third optical value higher than one or more other regions on the third surface of the third gemstone by analyzing the third three-dimensional model of the third gemstone; determining, by the one or more processors, a third diffractive structure to be arranged on the identified third region of the third surface of the third gemstone, such that the third gemstone with the third diffractive structure has a third higher optical performance than the third gemstone without the third diffractive structure; determining, by the one or more processors, a composite diffractive structure that is based in part on the first, second, and third diffractive structures and that is different than each of the first, second, and third diffractive structures; and applying the composite diffractive structure to fourth, fifth, and sixth gemstones that are different than the first, second, and third gemstones.

The composite diffractive structure can be suitable for diffracting light when applied to each of the fourth, fifth, and sixth gemstones and be not ideal for diffracting light when applied to any of the fourth, fifth, and sixth gemstones. The composite diffractive structure can be applied to the fourth, fifth, and sixth gemstones without obtaining a three-dimensional model of any of the fourth, fifth, and sixth gemstones. The composite diffractive structure can be applied to the fourth, fifth, and sixth gemstones prior to obtaining a three-dimensional model of any of the fourth, fifth, and sixth gemstones.

A sixteenth aspect of the present disclosure features a method of managing optical characteristics of a gemstone, the method including patterning a diffractive structure that includes a plurality of diffractive cuts on each of a plurality of facets of the gemstone, where each of the diffractive cuts is positioned in a high impact optical area with precisely controlled depth, pitch, and uniformity such that the diffractive cuts are invisible to a human eye without a jeweler's loupe, the diffractive cuts are invisible to the human eye with a jeweler's loupe, and the diffractive cuts diffract light in a way that is noticeable to the human eye without a jeweler's loupe.

A seventeenth aspect of the present disclosure features a method of managing optical characteristics of a gemstone, the method including patterning one or more diffractive structures on one or more facets of the gemstone, where each of the diffractive structures is positioned on a high impact optical region with precisely controlled depth, pitch, and uniformity such that the diffractive structures have little visibility or are invisible to a human eye without a jeweler's loupe, the diffractive structures have little visibility or are invisible to the human eye with a jeweler's loupe, and the diffractive structures diffract light in a way that is noticeable to the human eye without a jeweler's loupe. The facets with the patterned diffractive structures are not opposite to each other. The number of the facets with the patterned diffractive structures can be no more than a half of a total number of facets of the gemstone. For example, if the gemstone has 8 facets, the number of the facets with the patterned diffractive structures can be 1, 2, 3, or 4.

The details of one or more implementations of the subject matter of this disclosure are set forth in the accompanying drawings and associated description. Other features, aspects, and advantages of the subject matter will become apparent from the description, the drawings, and the claims.

DESCRIPTION OF DRAWINGS

FIG. 4 shows an example showing associations between diffractive structure settings and ranges of gemstone characteristics.

DETAILED DESCRIPTION

Figure 1A:
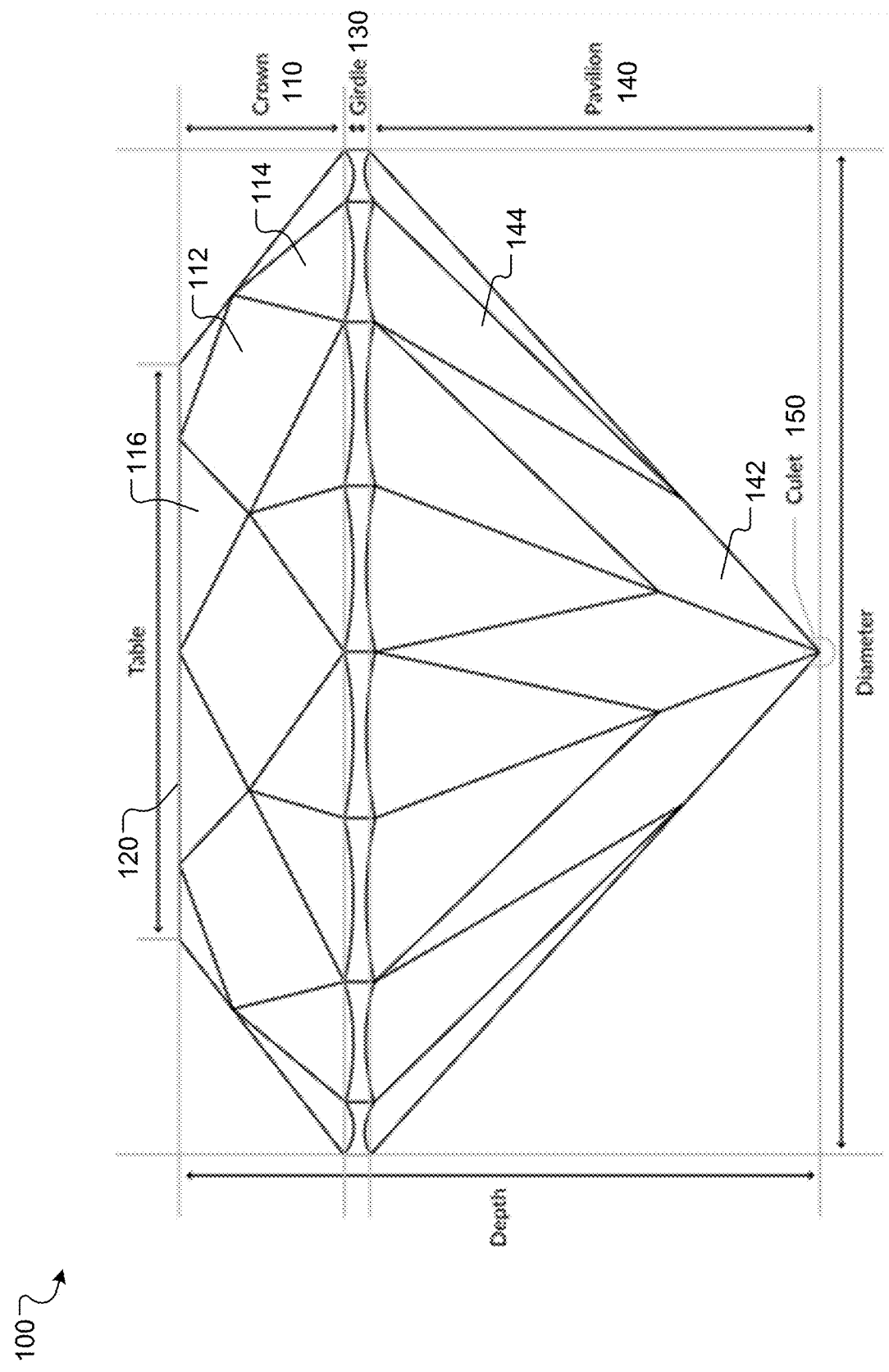
FIG. 1A is a schematic diagram of a round brilliant cut diamond as an example gemstone.

Implementations of the present disclosure provide methods for fabricating diffractive structures on gemstones for high optical performance (e.g., brilliance, fire, and/or scintillation). An algorithm, a recipe or a process can be developed, which can be practical and commercially viable from a performance and cost standpoint. As starting points, 3D modeling, simulation, and/or fabrications can be utilized to help identify high optical value regions and/or to determine corresponding diffractive structures on representative gemstones. Then the locations, shapes, and/or sizes of high optical value regions on the representative gemstone can be used to determine high-optical-value (HOV) regions on other gemstones having similar geometry to the representative gemstone. Thus, there is no need to develop a respective 3D model for each gemstone to be fabricated with diffractive structures, which can greatly improve processing speed and be cost-effective.

For example, a database can be developed to store information of different representative gemstones having different geometries. The database can store and associate respective diffractive structure settings for gemstones with different geometries or different combinations of ranges of gemstone characteristics. The diffractive structure settings and the combinations can be determined based on the information of the representative gemstones, the determined HOV regions, and the determined diffractive structures.

Each diffractive structure setting can include information of a plurality of facets of a gemstone to be fabricated with diffractive structures, information of a respective HOV region on each of the plurality of facets, and/or information of a respective diffractive structure to be fabricated in the respective HOV region on each of the plurality of facets. The information of the respective diffractive structure can include one or more of parameters of the respective diffractive structure including a depth, a pitch, uniformity, a shape, an angle, a size, and a number of cuts. The information of the respective HOV region on each of the plurality of facets can include a relative location of the respective HOV region on the facet, a shape of the respective HOV region, and/or a relative size of the respective HOV region to the facet. Prior technology utilized as many gratings to as many facets to improve light performance of gemstones. However, the large number of gratings interfered with beams of light within the gemstone and generated marginal light performance improvement. A particular number of facets can be selected from the total facets of the gemstone to be fabricated with diffractive structures. For example, the selected facets are not opposite to each other. The total number of facets of the gemstone can be 8, e.g., for a round brilliant diamond, and the number of the selected facets can be 4. The gemstone includes first, second, third, fourth, fifth, sixth, seventh, and eighth facets, and the selected facets can include first, second, third and fourth facets, first, second, third, and eighth facets, first, second, fourth, and seventh facets, first, third, fourth and sixth facets, or first, third, sixth, and eighth facets. The technique applying diffractive structures on facets that are not opposite to each other can be also implemented in a gemstone having any other suitable shape such as square princess.

For a new gemstone to be processed, a corresponding representative gemstone or diffractive structure setting can be selected from the database based on a geometry or multiple gemstone characteristics of the new gemstone. Then, a corresponding diffractive structure setting, including particular facets, HOV regions on the particular facets, and diffractive structures on the particular facets, can be determined based on the corresponding diffractive structure setting and the geometrical information of the new gemstone.

The technologies described herein are based on in-depth knowledge of optical performance of each gemstone, the determination of location of high value optical regions, the understanding of the dynamics of light beams and the ability to steer light to a human eye. Focused ion beam (FIB) can be utilized to improve the control of precise cutting of diffractive structures on gemstones. Impregnated ions remaining in the diffractive structure can be removed by heating the gemstones to a temperature in a predetermined range in a container (e.g., an oven) having substantially little or no oxygen (e.g., by purging inert gas). The predetermined range can be from 1000 to 1300 degree Fahrenheit, particularly from 1100 to 1200 degree Fahrenheit. In this way, the remaining ions in the diffractive structures can be invisible to the human eye or even with a jewelry's loupe (e.g., 10× or 30× magnification).

In some implementations, the FIB machine can include the database for diffractive structure settings associated with different combinations of ranges of gemstone characteristics and/or fabrication recipes. When characteristics of a gemstone is provided to the FIB machine, the FIB machine can search the database to identify a particular diffractive structure setting for the gemstone, or an operator can pick or change one of the diffractive structure settings based on the characteristics of the gemstone. Then the FIB machine can automatically identify HOV regions (including locations, shapes and/or sizes) on selected facets for the gemstone and/or determine corresponding diffractive structures. In such ways, an automatic or semi-automatic process can be achieved.

The technologies can significantly improve the speed and control of the manufacturing process, standardize process methodology to improve quality and placement of the diffractive structures on the gemstones. Higher light performance and significantly lower processing costs can be achieved to support broad based commercialization of the new technologies.

The technologies can optimize diffractive structures for any diamond, e.g., hand-cut or semi-automated cut, in an automated or semi-automated fashion, which makes it able to deal with natural variations of diamonds. The technologies can minimize patterned areas for maximum optical performance, which enables to lower the manufacturing cost of improving a diamond's light performance to a higher level and provide higher retail value for sellers as well as a higher customer value in the market.

Process outcomes can be further improved by incorporating other methods, e.g., by using high quality generation equipment and controlling diamond intake performance specifications. For example, diamonds to be processed need to be measured and satisfy a minimum performance threshold. After diamonds are processed, optical performance of the diamonds is measured to see whether it reaches the minimum performance threshold. The optical performance can be graded based on scintillation (or sparkle) scaling.

The technologies described herein can be applied to any material whose aesthetic appearance can be enhanced by beam steering effects, diffractive effects, and/or dispersive effects of diffractive structures. For example, the technologies can be applied to any suitable type of gemstone, including lab grown diamonds, synthesized diamonds, or any other synthetics, natural and artificial diamond stimulants and clear stones such as cubic zirconium, zircon, moissanite, topaz, rutile, strontium titanate, spinel, yttrium aluminum garnet, strontium titanate, yttrium aluminum garnet (YAG), gadolinium gallium garnet (GGG), and glass to name only a few examples. The methods could also be applied to other items of jewelry, whether optically transmissive or not (e.g., reflective diffractive structures could be used on opaque materials). The materials can be raw or have undergone any suitable processing such as partially cut, well cut, poorly cut, round cut, princess-cut, octagonal step-cut, unpolished, partially polished, or polished. The materials can also have any desired shape or size. For illustration purposes only, some examples in the following description are directed to round brilliant cut diamonds.

FIG. 1A is a schematic diagram of a round brilliant cut diamond 100 as an example gemstone. An upper portion of the round brilliant cut diamond 100 is a crown 110. The crown 110 includes a flat top portion called table 120. A lower portion of the round brilliant cut is a pavilion 140, whose tip is called a culet 150. The crown 110 and the pavilion 140 are separated by a flat girdle 130 with a width to help prevent chipping that might otherwise occur if the crown 110 and pavilion 140 are joined at a sharp angle. The crown 110 includes a number of surrounding facets including upper main facets 112, upper girdle facets 114, and star facet 116. The pavilion 140 includes a number of facets including lower main facets 142 and lower girdle facets 144.

The diamond 100 has a diameter defined by opposite edges of the girdle 130. The diamond 100 has a depth extending from the culet 150 to the top surface of the table 120. A geometry of the diamond 100 can include the diameter and the depth.

Figure 1B:
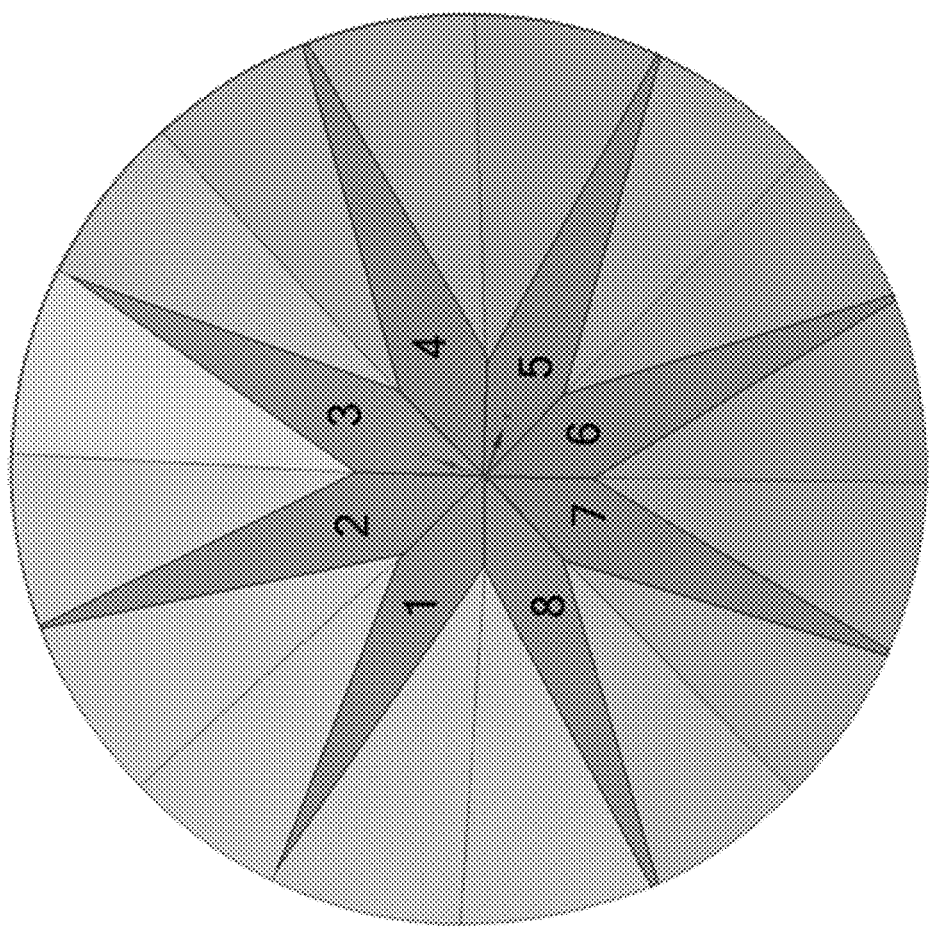
FIG. 1B shows a schematic diagram of eight lower main facets on a pavilion of a diamond.

FIG. 1B shows a schematic diagram of eight lower main facets on the pavilion 140 of FIG. 1A. The eight lower main facets are numbered as 1 to 8. The eight facets form four pairs of facets, including 1 and 5, 2 and 6, 3 and 7, and 4 and 8. On a planar view of the pavilion, the two facets in one pair are opposite to each other.

In some cases, all the eight facets can be selected to be arranged with diffractive structures. In some cases, a less number of the eight facets can be selected to be arranged with diffractive structures. Particularly, since a light diffracted from a facet can travel to the opposite facet and reflected by the opposite facet, one facet from a pair of facets can be selected to be arranged with a diffractive structure, and the other facet from the same pair can be left blank without arranging a diffractive structure, which can double the effect of the diffractive structure and minimize the light loss. In such a way, less number of diffractive structures can be determined and fabricated on the diamond, which can reduce cost and/or improve the optical performance of the diamond.

Figure 1D:
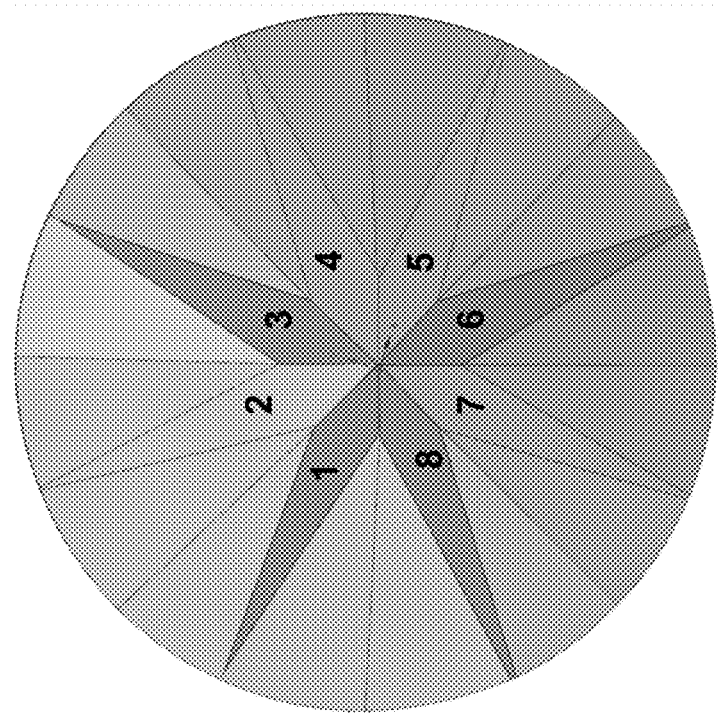
FIG. 1D shows another example of four lower main facets selected for diffractive structures.
Figure 1C:
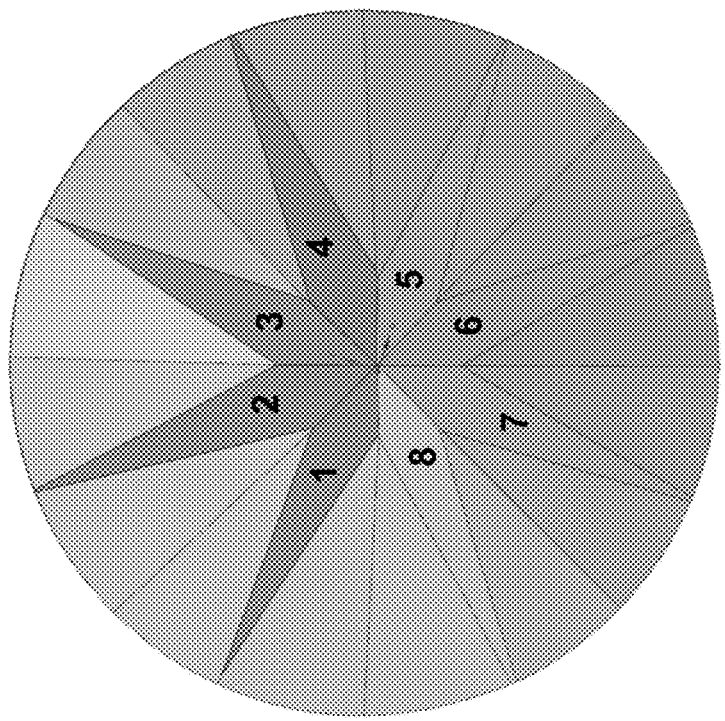
FIG. 1C shows an example of four lower main facets selected for diffractive structures.

For example, for the eight lower main facets, four facets from the four pairs can be selected, as illustrated in FIGS. 1C and 1D. There can be different combinations of the four selected facets, for examples, facets 1, 2, 3, and 4 (as shown in FIG. 1C), facets 1, 2, 3, 8, facets 1, 2, 4, 7, facets 1, 3, 4, 6, and facets 1, 3, 6, 8 (as shown in FIG. 1D). Since the diffracted light from a facet can travel to the opposite facet and possibly to an adjacent facet, to maximize the optical performance of the diamond, the four selected facets can be evenly contributed around the diamond or the light reflection in the diamond can be balanced or uniformly distributed.

Figure 2B:
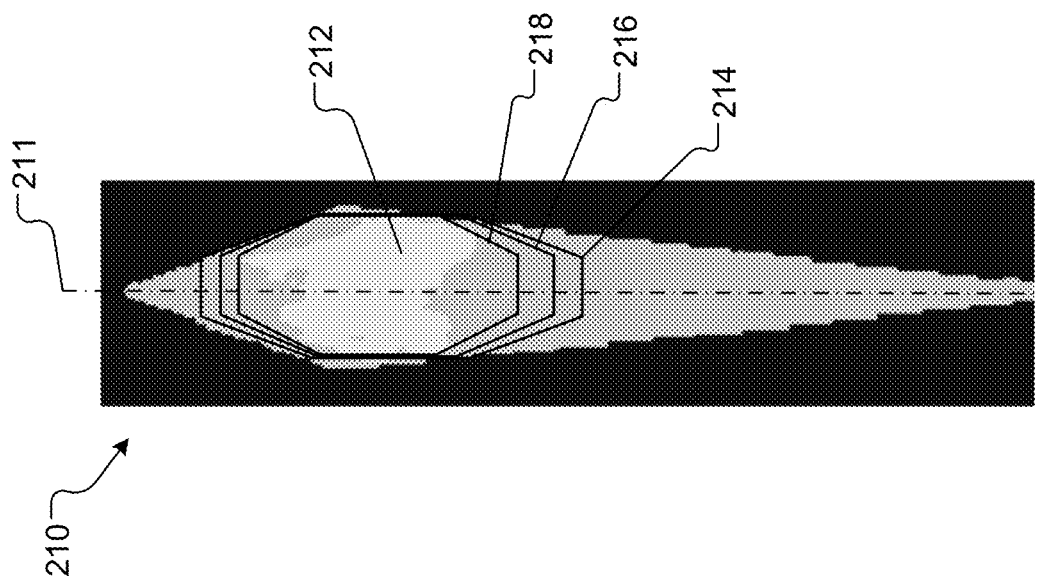
FIG. 2B is a schematic diagram showing a process of optimizing a region on a facet of a diamond to approximate the high optical value region.
Figure 2A:
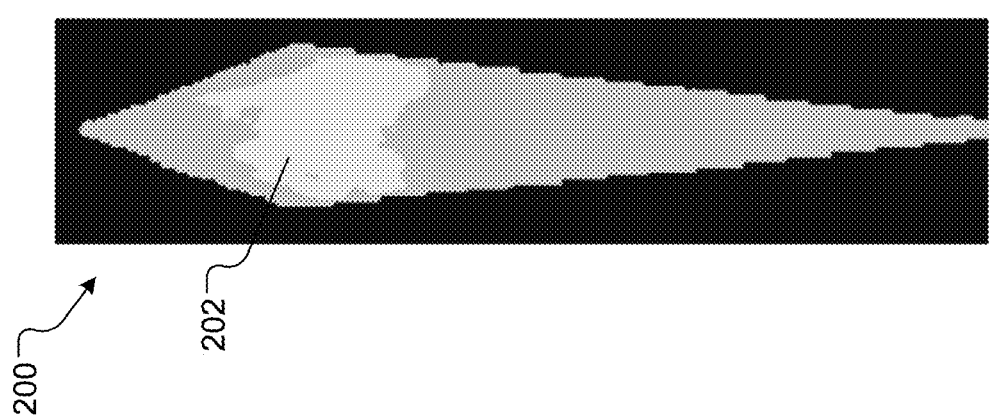
FIG. 2A shows an example high optical value (HOV) region on a facet of a representative diamond determined by using three-dimensional (3D) modelling and simulation.

FIG. 2A shows an example high optical value region on a facet of a diamond. The high optical value region can be determined by using three-dimensional (3D) modeling, simulation, and/or fabrication as described in a U.S. Provisional Patent Application Ser. No. 62/540,844, entitled "MANAGING OPTICAL PERFORMANCE OF GEMSTONES WITH DIFFRACTIVE STRUCTURES" and filed on Aug. 3, 2017, whose content is hereby incorporated by reference in its entirety. In some implementations, the high optical value region can be also determined by other suitable modelling and/or simulation methods, e.g., ray tracing methods.

Figure 6:
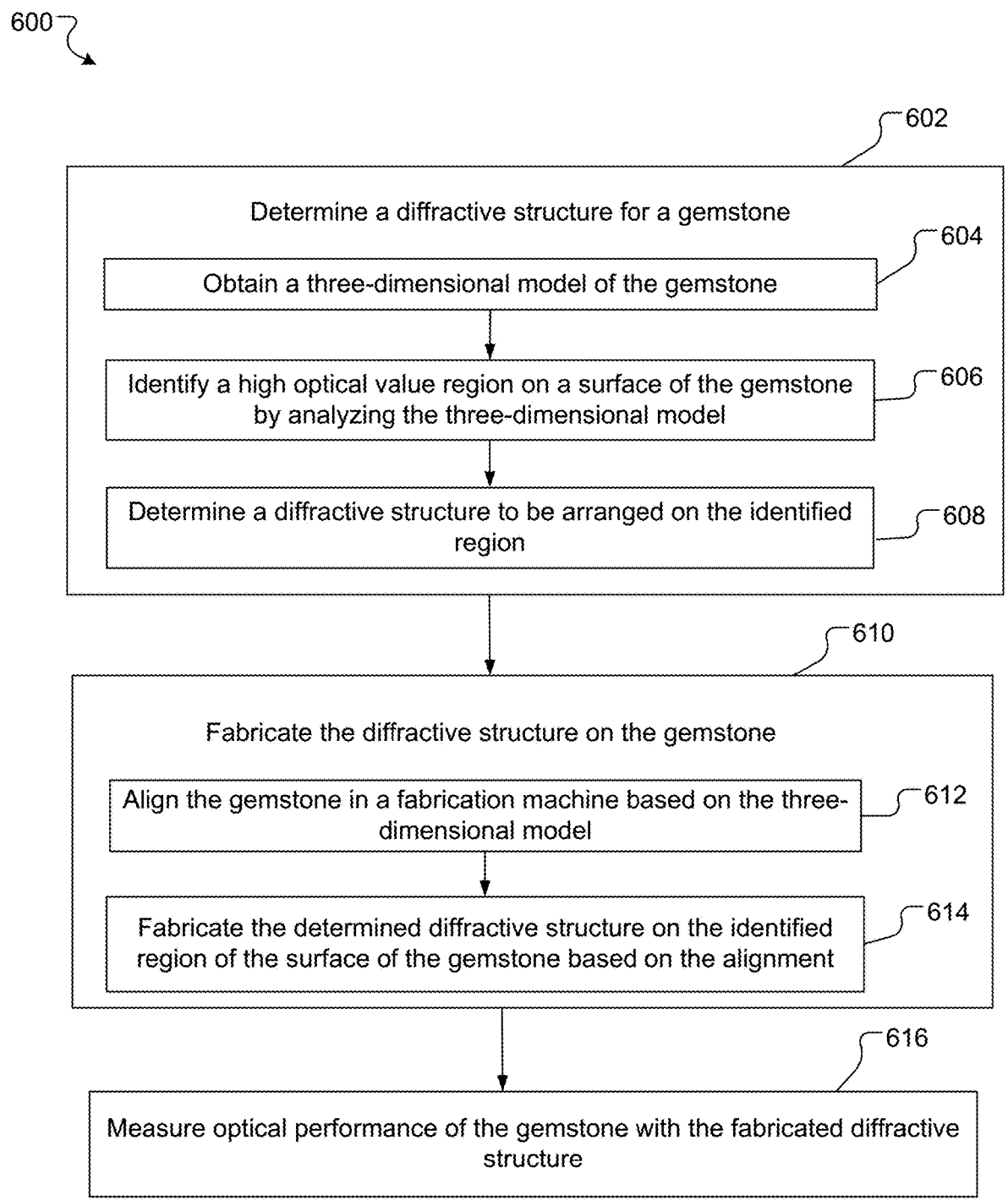
FIG. 6 is a flowchart of an example process of determining a diffractive structure on a high optical value region of a gemstone using 3D modelling and simulation.

As discussed with further details in FIG. 6, a 3D model of the diamond can be first obtained, and the high optical value region can be identified on the facet of the diamond by analyzing the 3D model. In the analysis, propagation of an incident light through the diamond and reflected by the facet is simulated and irradiance data representing light reflection distribution of the light on the facet can be generated. The high optical value region can be then determined based on the generated irradiance data representing the light reflection distribution on the facet. The high optical value region has an optical value higher than one or more other areas on the facet of the diamond. The optical value can be defined as a ratio of an energy enclosed in the high optical value region and a total energy enclosed in the corresponding surface in the irradiance data.

FIG. 2A show example irradiance (power per area) plots 200 representing light reflection distribution on the facet, by analyzing the 3D model of the diamond. It is shown that a region 202 encloses most of the energy. That is to say, on the facet, the light is reflected most by the region 202. Thus, if a diffractive structure is arranged on the region 202, the diffractive structure can have a most significant effect on the optical performance of the diamond. As discussed with further details in FIG. 6, the diffractive structure can be also determined by 3D modelling and simulation and/or fabrication. The region 202 is identified to have a higher optical value than one or more other regions on the facet and thus can be determined to be arranged with a diffractive structure. As an example, the optical value of the region 202 is about 70%. A maximum irradiance of the selected facet lies at a center of the region 202. The center is closer to the culet of the diamond than the girdle of the diamond. In a particular example, the center of the region 202 is about 1 mm away from the culet.

The diamond in FIG. 2A can be used as a representative diamond. A diamond to be processed having a similar geometry to the representative diamond can use information of the high optical value region 202 of the representative diamond to determine its own high optical value region, without obtaining and simulating its own 3D model. A diffractive structure to be fabricated on the high optical value region of the diamond can have the substantially same properties as those of the diffractive structure determined for the high optical value region 202 of the representative diamond. The properties can include a period, a depth, a width, an orientation, a shape, a blaze angle, and a number of cuts. Information of the representative diamond, including respective high optical value regions on the facets and respective diffractive structures to be arranged on the high optical value regions, can be stored in a database. Geometry or dimensional data of a diamond to be processed can be compared with those of representative diamonds in the database. Based on the comparison result, a particular representative diamond corresponding to the diamond to be processed can be selected.

FIG. 2B is a schematic diagram showing a process 210 of optimizing a region on a facet of a diamond to approximate a high optical value region, without using a 3D model of the diamond. The facet extends along an axis 211 from the culet of the diamond to the girdle of the diamond. The diamond has a similar geometry to the representative diamond in FIG. 2A. Based on information of the high optical value region 202 of the representative diamond, a corresponding particular region 212 can be determined on the facet of the diamond. In some examples, a diameter of the diamond is proportional to a diameter of the representative diamond, and/or a depth of the diamond is proportional to a depth of the representative diamond. The particular region 212 can have a size proportional to the high optical value region 202 and a location corresponding to the location of the high optical value region 202 on the facet of the representative diamond.

As shown in FIG. 2B, the particular region 212, similar to the high optical value region 202 of FIG. 2A, may have an irregular shape (or contour), which makes it hard to fabricate a diffractive structure on the facet to maximize the optical performance of the diamond. Also, the particular region 212 may not be exactly the high optical value region on the facet of the diamond, because each diamond has a unique property and different from other diamonds at a certain degree. However, this particular region 212 can be a starting point to locate the high optical value region on the facet of the diamond.

Figure 3:
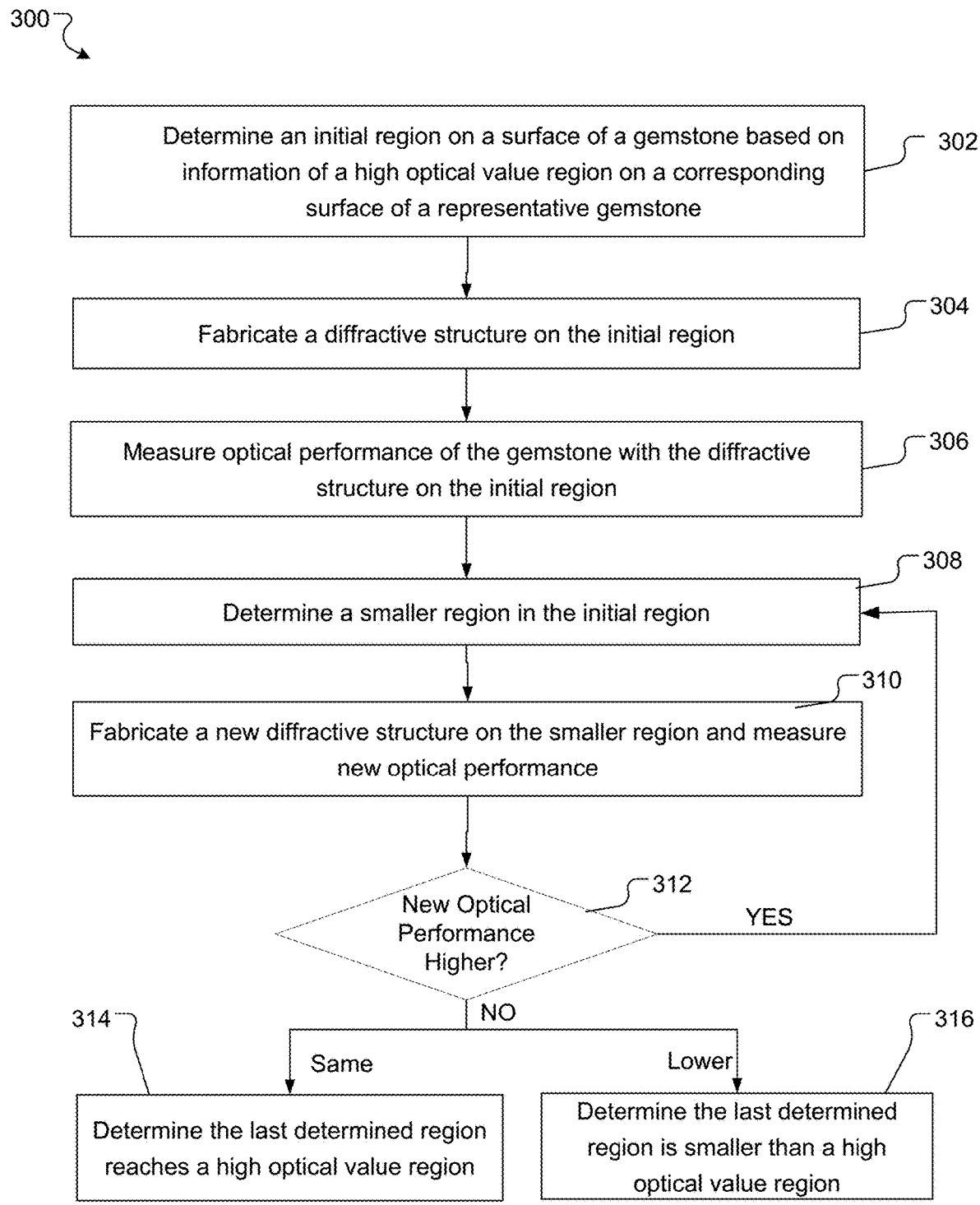
FIG. 3 is a flowchart of an example process of determining a high optical value (HOV) region on a surface of a gemstone.

As discussed with further details in FIG. 3, the process 210 can be executed to approximate the high optical value region based on the particular region 212, e.g., using a repetitive method. As illustrated in FIG. 2B, an initial region 214 is determined to be large enough to encompass the particular region 212. The initial region 214 can be as large as possible on the facet, so that it can be guaranteed that the high optical value region is included in the initial region 214. It can have any desired shape, e.g., an eight-sided polygon as illustrated in FIG. 2B. Then a first diffractive structure is fabricated on the initial region 214 and first optical performance of the diamond with the first diffractive structure on the initial region 214 is measured. The first optical performance can be evaluated by at least one of brilliance, fire, and scintillation.

In some cases, the first optical performance can be compared to a predetermined threshold. The predetermined threshold can be set as a minimum acceptable standard. If the first optical performance is lower than the predetermined threshold, the process 210 continues. If the first optical performance is higher than the predetermined threshold, the process 210 can be stopped or continue to further optimize the optical performance.

On one hand, a larger region can guarantee coverage of the high optical value region to positively affect the optical performance of the diamond; on the other hand, a large number of cuts in the larger region on the facet can negatively affect the optical performance of the diamond and increase the processing cost. Thus, the high optical value region may be located by balancing the two effects.

A second region 216 can be determined based on the measured first optical performance. For example, the size of the second region 216 can be determined based on a comparison of the first optical performance and the predetermined threshold. As illustrated in FIG. 2B, the second region 216 can be within the initial region 214 and still include the particular region 212. As the particular region 212 extends almost fully along a direction perpendicular to the axis 211, the second region 216, similar to the initial region 214, can extend fully along this direction to cover the particular region 212. Along the axis 211, the second region 216 can extend shorter than the initial region 214. The second region 216 can extend shorter on one end or on both ends. In some cases, if the particular region 212 does not extend fully along the direction perpendicular to the axis 211, the first and second regions 216 can also be adjust along the direction.

The diamond with the first diffractive structure can be polished to remove the first diffractive structure. Then a second diffractive structure can be fabricated on the second region 216 on the facet of the diamond. The second diffractive structure can have the same properties as the first diffractive structure, except that the second diffractive structure has a smaller size, that is, a less number of cuts. In some cases, the second diffractive structure can be added above the first diffractive structure without polishing to remove the first diffractive structure. Then second optical performance of the diamond with the second diffractive structure can be measured. The second optical performance can be compared to the first optical performance. If the second optical performance is higher than the first optical performance, it may indicate that the high optical value region is still included in the second region 216 and further optimization can be executed. If the second optical performance is lower than the first optical performance, it may indicate that the second region 216 is too small and needs to be adjusted to be larger. If the second optical performance is substantially identical to the first optical performance, it may indicate that the second region 216 approaches the high optical value region and no further optimization is needed. The second region 216 can be considered as the high optical value region for the facet of the diamond.

A third region 218 can be determined based on the second optical performance and/or the first optical performance and/or the predetermined threshold. The third region 218 can be further decreased, e.g., along the axis 211 and/or along the direction perpendicular to the axis 211. The third region 218 can be included in the second region 216. In some cases, the third region 218 still encompasses the particular region 212. In some cases, the third region 218 may not fully cover or encompass the particular region 212.

Similarly, the diamond with the second diffractive structure can be polished to remove the second diffractive structure. Then a third diffractive structure can be fabricated on the third region 218 on the facet of the diamond. The third diffractive structure can have the same properties as the first or second diffractive structure, except that the third diffractive structure has a smaller size, that is, a less number of cuts. In some cases, the third diffractive structure can be added above the second diffractive structure without polishing to remove the second diffractive structure. Then third optical performance of the diamond with the third diffractive structure can be measured.

The third optical performance can be compared to the second optical performance. If the third optical performance is higher than the second optical performance, it may indicate that the high optical value region is still included in the third region 218 and further optimization can be executed. If the third optical performance is lower than the second optical performance, it may indicate that the third region 218 is too small and needs to be adjusted to be larger (but still within the second region 216). If the third optical performance is substantially identical to the second optical performance, it may indicate that the third region 218 approaches the high optical value region and no further optimization is needed. The third region 218 can be considered as the high optical value region for the facet of the diamond.

The process 210 can iterate the steps until no further improvement on the optical performance of the diamond can be achieved. Then, the last determined region can be determined to be the high optical value region for the facet of the diamond.

The diamond with the determined high optical value region can be considered as another representative diamond. Information of the diamond, including the high optical value region on the facet and the geometry of the diamond, can be stored in the database storing other representative diamonds for further reference. FIG. 3 is a flowchart of an example process 300 of determining a high optical value region on a surface of a gemstone. The process 300 can be used to implement the process 210.

An initial region on a surface of a gemstone is determined based on information of a high optical value region on a corresponding surface of a representative gemstone (302). The gemstone has a geometry similar to, e.g., proportional to, a geometry of the representative gemstone. In some examples, the gemstone is a diamond having a culet, a pavilion, a girdle, a crown, and a table, and the surface is a pavilion lower main facet extending along a direction from the culet to the girdle. The geometry of the first gemstone can include a height of the facet, a diameter of the diamond, and a depth of the diamond.

The high optical value region on the corresponding surface of the representative gemstone corresponds to a particular region on the surface of the gemstone, and the initial region includes the particular region, as shown in FIG. 2B. The initial region can encompass the particular region. The initial region can be substantially larger than the particular region to guarantee that the high optical value region for the surface of the gemstone is within the initial region. The size of the first region can be larger than the size of the particular region by a particular percent, and the particular percent can be larger than 10%, 20%, 30%, 40%, 50%, 60%, 70%, 80%, 90%, or 100%. The first region on the surface does not overlap with adjacent surface (or facet).

In some cases, as discussed above, the high optical value region on the corresponding surface of the representative gemstone can be determined by 3D modelling and simulation and/or fabrication. A particular diffractive structure to be arranged on the high optical value region of the corresponding surface of the representative gemstone can be also determined by the 3D modelling and simulation and/or fabrication, such that the representative gemstone with the particular diffractive structure has a higher optical performance than the representative gemstone without the particular diffractive structure. The particular diffractive structure can be optimized to achieve the highest optical performance by simulation. The initial region on the surface of the gemstone can be determined without obtaining a 3D model of the gemstone.

A diffractive structure is fabricated on the surface of the gemstone (304). The diffractive structure can have the substantially same properties as the particular diffractive structure for the high optical value region of the representative gemstone. In some examples, the diffractive structure includes a diffraction grating having a property defined by one or more parameters including a period, a depth, a width, an orientation, a shape, and a blaze angle. An edge of the initial region can define a boundary of the diffractive structure. A number of cuts of the diffractive grating can be related to the size of the initial region.

Optical performance of the gemstone with the diffractive structure on the initial region is measured (306). The optical performance can include at least one of brilliance, fire, or scintillation.

A smaller region in the initial region is determined based on the optical performance (308). The smaller region can still include the particular region, as illustrated in FIG. 2B. For example, the optical performance can be compared to a predetermined threshold. The predetermined threshold can be a minimum acceptable optical performance or a maximum optical performance. The size of the smaller region decreased from the initial region can be based on the difference between the optical performance and the predetermined threshold. The size of the smaller region can be smaller than the size of the initial region by a percent. The percent can be 5%, 10%, 15%, or 20%.

A new diffractive structure is fabricated on the smaller region and new optical performance is measured (310). The new diffractive structure on the smaller region can have the substantially same property as the diffractive structure on the initial region. As the number of cuts is defined by the size of the region, the new diffractive structure can have less cuts than the diffractive structure fabricated on the initial region.

It is determined whether the new optical performance is higher than the previous optical performance (312). If the new optical performance is higher than the previous optical performance, it indicates that the high optical value region for the surface of the gemstone is still within the smaller region. The process 300 returns to step 308 to further decrease the region size to approximate the high optical value region.

If the new optical performance is substantially same as the previous optical performance, it is determined that the last determined region reaches the high optical value region (314). The process 300 ends. If the new optical performance is smaller than the previous optical performance, it is determined that the last determined region may be smaller than the high optical value region (316). The process 300 can increase the last determined region to continue the optimization process.

In some implementations, the new optical performance is compared to the predetermined threshold. If the new optical performance is smaller than the predetermined threshold, a third region can be determined. The third region can be in the last determined region and include the particular region. If the new optical performance is substantially the same or higher than the predetermined threshold, the last determined region can be considered as the high optical value region. No more optimization process is performed.

In some cases, the predetermined threshold can be set to be higher than an optical performance of the gemstone without diffractive structure by a predetermined percent. The predetermined percent can be 50%, 55%, 60%, 70%, 75%, 80%, 85%, 90%, 95%, or 100%.

In some cases, the predetermined threshold is determined based on a particular optical performance of the representative gemstone with a particular diffractive structure arranged on the high optical value region on the corresponding surface of the representative gemstone.

In some implementations, the process 300 is also used to determine a high optical value region on a surface of another gemstone to be processed that has a similar property to the representative gemstone. In some implementations, two or more surfaces of the gemstone are configured to be fabricated with a diffractive structure. For example, as illustrated in FIGS. 1C and 1D, four facets of a diamond can be selected to be fabricated with diffractive structures. The process 300 can be then used to determine a respective high optical value (HOV) region for each of the surfaces by using a representative gemstone. Different surfaces of the gemstone can have the same representative gemstone or different representative gemstones.

A diffractive structure setting can be determined to include information of the selected surfaces of the gemstone, information of the determined respective HOV regions on the selected surfaces, and information of the respective diffractive structures to be fabricated on the respective HOV regions on the selected surfaces. The information of the diffractive structure can include one or more of parameters of the respective diffractive structure including a depth, a pitch, uniformity, a shape, an angle, a number of cuts, and a space (or a width) of individual cuts. The information of the respective high-optical-value (HOV) region on each of the selected surfaces can include a relative location of the respective HOV region on the surface, a shape of the respective HOV region, and a relative size of the respective HOV region to the surface.

The geometrical information of the gemstone can be obtained. For example, if the gemstone is a diamond, and the geometrical information can include one or more of gemstone characteristics including a crowned percentage, a table percentage, a depth proportion, a joint angle between a crown and a pavilion, and symmetry. The diffractive structure setting can be associated with the geometrical information of the gemstone. The diffractive structure setting can be also associated with ranges of gemstone characteristics, where the geometrical information of the gemstone is within the respective ranges of gemstone characteristics. The ranges can be determined by empirical results and/or theoretical results and/or simulation results.

In some implementations, the process 300 can be performed on a number of gemstones. Diffractive structure settings and associated ranges of gemstone characteristics can be determined by analyzing the results of the processes on the number of gemstones. For example, the results associated with gemstones with similar geometrical information (or a family of gemstones) can be analyzed together to determine a corresponding diffractive structure setting and associated ranges for gemstone characteristics.

FIG. 4 shows an example showing associations between diffractive structure settings and ranges of gemstone characteristics. The associations can be stored within a repository or database. For each diffractive structure setting, it is associated with respective ranges for each of gemstone characteristics. For example, setting 1 is associated with a first combination of range R11 for a first characteristic C1, range R12 for a second characteristic C2, . . . Setting 2 is associated with a second combination of range R21 for the first characteristic C1, range R22 for the second characteristic C2, . . . Similarly, setting n is associated with a n-th combination of range Rn1 for the first characteristic C1, range Rn2 for the second characteristic C2, . . . The combinations are different from each other, although the ranges for characteristics may be the same or different in different combinations. For example, R11 and R21 can be the same, but R12 and R22 can be different. For illustration purposes only, two or more gemstone characteristics are listed. However, it is understandable that each setting can be associated with just one gemstone characteristic.

Figure 5A:
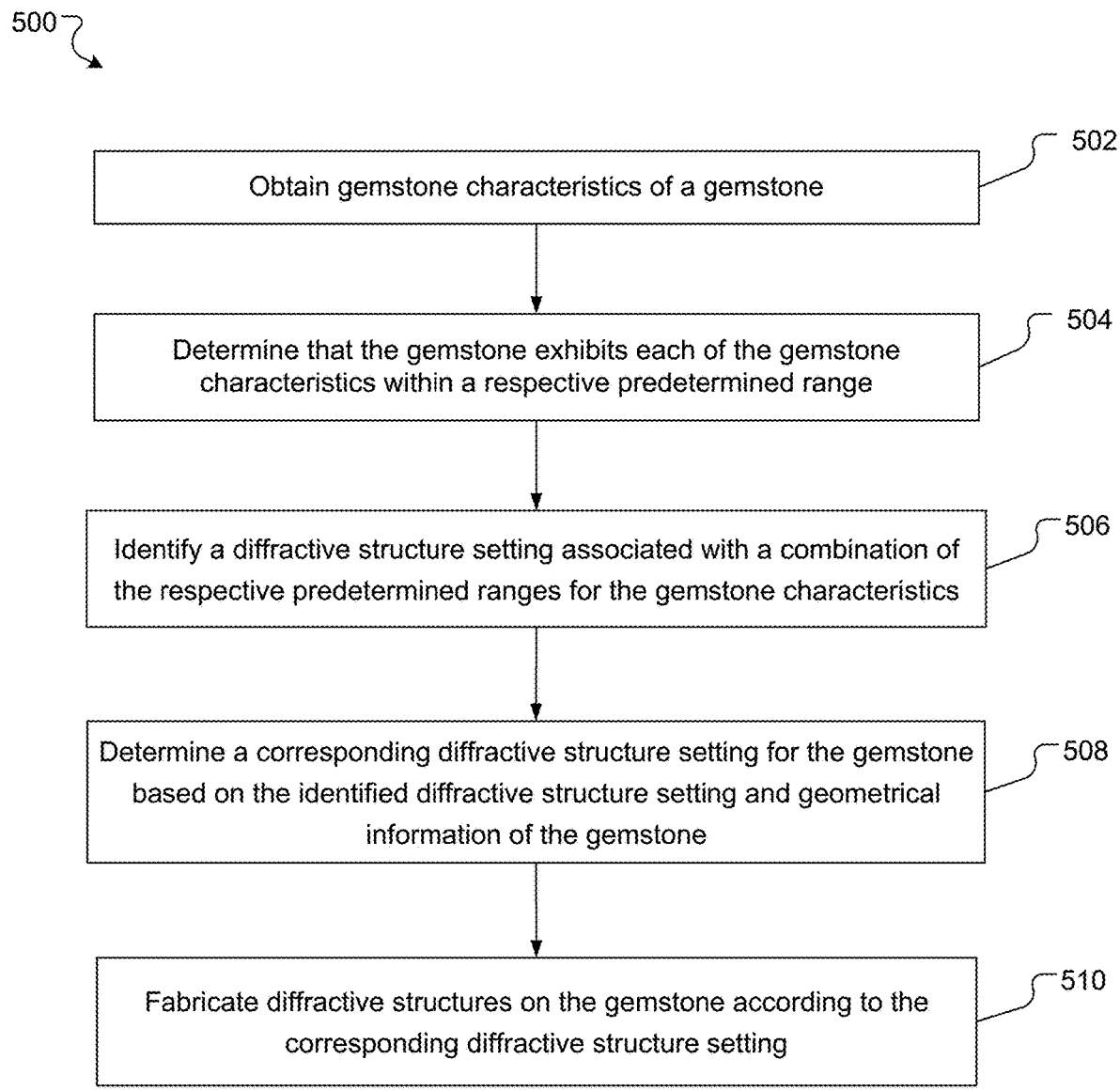
FIG. 5A is a flowchart of an example process of managing diffractive structures on a gemstone for high optical performance.

As discussed with further details in FIG. 5A, a process can be developed to fabricate diffractive structures on gemstones for high optical performance by using the repository including the associations between different diffractive structure settings and ranges of gemstone characteristics (as illustrated in FIG. 4), without using 3D model simulation as illustrated in FIG. 6 and without using repetitive process as illustrated in FIG. 2B or FIG. 3.

FIG. 5A is a flowchart of an example process 500 of fabricating diffractive structures on a gemstone for high optical performance. The process 500 can be performed by a fabrication machine, e.g., a focused-ion-beam (FIB) machine, a micro- or nano-patterning machine such as micro- or nano-lithography system, or any suitable machine or system, in a semi-automatic or fully-automatic manner.

Gemstone characteristics of a gemstone is obtained (502). The gemstone can be a diamond. The gemstone characteristics can include one or more of a crown percentage, a table percentage, a depth proportion, and a joint angle between a crown and a pavilion. The gemstone characteristics can be determined based on geometrical information of the gemstone, for example, a height of the facet, a diameter of the diamond, and a depth of the diamond. In some cases, the gemstone is a cut diamond, the gemstone characteristics can be obtained based on geometrical cut parameters of the cut diamond. In some cases, the gemstone characteristics can be obtained based on a 3D model of gemstone. In some cases, the gemstone characteristics can be obtained based on geometrical measurement of an outer surface of the gemstone.

It is determined that the gemstone exhibits each of the gemstone characteristics within a respective predetermined range (504). The predetermined ranges of the gemstone characteristics are associated with respective diffractive structure settings, as illustrated in FIG. 4. For example, if there are two gemstone characteristics C1 and C2, the process 500 determines that the gemstone exhibits a first gemstone characteristic C1 in a first predetermined range, e.g., R21, and a second gemstone characteristic C2 in a second predetermined range, e.g., R22.

A diffractive structure setting associated with a combination of the respective predetermined ranges for the gemstone characteristics is identified (506). The repository can be searched based on the combination of the respective predetermined ranges for the gemstone, and the associated diffractive structure setting can be identified. For example, if the gemstone exhibits the first gemstone characteristic C1 in range R21 and the second gemstone characteristic C2 in range R22, the diffractive structure setting 2 in the repository can be identified. In some cases, an operator can select the diffractive structure setting from a plurality of diffractive structure settings stored in the repository based on the gemstone characteristics of the gemstone. The fabrication machine can identify the diffractive structure setting from the selection of the operator.

As noted above, the diffractive structure setting can include information of facets of the gemstone selected to be fabricated, information of the determined respective HOV regions on the selected surfaces, and information of the respective diffractive structures to be fabricated on the respective HOV regions on the selected surfaces. The information of the diffractive structure can include one or more of parameters of the respective diffractive structure including a depth, a pitch, uniformity, a shape, an angle, and a number of cuts. The information of the respective high-optical-value (HOV) region on each of the selected surfaces can include a relative location of the respective HOV region on the surface, a shape of the respective HOV region, and a relative size of the respective HOV region to the surface.

A corresponding diffractive structure setting for the gemstone is determined based on the identified diffractive structure setting and geometrical information of the gemstone (508). The corresponding diffractive structure setting can be adjusted based on the identified diffractive structure setting according to the geometrical information of the gemstone. The corresponding diffractive structure setting for the gemstone can include the actual selected facets, the actual sizes/shapes/locations of the HOV regions on the selected facets, and the diffractive structures with actual values. The determination of diffractive structure placement and/or size can be determined by the geometrical information of the gemstone.

Diffractive structures are fabricated by the fabrication machine on the gemstone according to the corresponding diffractive structure setting (510). A respective diffractive structure can be fabricated on the corresponding HOV region on each of the selected facets. In some implementations, the fabrication of a diffractive structure (e.g., a grating) is controlled to reach a predetermined value of at least one of parameters of the diffractive structure. The parameters can include a depth, a pitch, uniformity, a shape, an angle, and a number of cuts. The fabrication can be controlled to achieve a predefined quality, e.g., a predefined depth, a predefined pitch, a predefined uniformity, a predefined shape, a predefined angle, and/or a predefined number of cuts. In some implementations, the quality of each cut/line that is cut into the surface of the gemstone can be controlled to achieve a defined pitch, depth, spacing, and design of each line of the grating. Each gemstone has unique geometry proportions that influences the characteristics of cut lines to optimize the light performance.

After fabricating a diffractive structure on a first selected facet of the gemstone, the gemstone can be aligned with respect to the fabrication machine such that a second HOV region on a second facet of the gemstone is matched to where the fabrication machine writes a corresponding second diffractive structure. The second facet is not opposite to the first facet. Then, the fabrication machine fabricates the corresponding second diffractive structure on the second HOV region on the second facet of the gemstone. The fabrication machine can perform a loop to fabricate multiple diffractive structures on multiple selected facets on the gemstone. In some examples, the gemstone is a diamond having a culet, a pavilion, a girdle, a crown, and a table, and the facet is a pavilion lower main facet extending along a direction from the culet to the girdle. The selected facets for the fabrication of the diffractive structures are four pavilion lower main facets, which are not opposite to each other.

If each of a plurality of gemstones exhibits the gemstone characteristics within respective predetermined ranges that are associated with a same diffractive structure setting, diffractive structures can be fabricated on each of the gemstones according to the same diffractive structure setting.

Figure 5B:
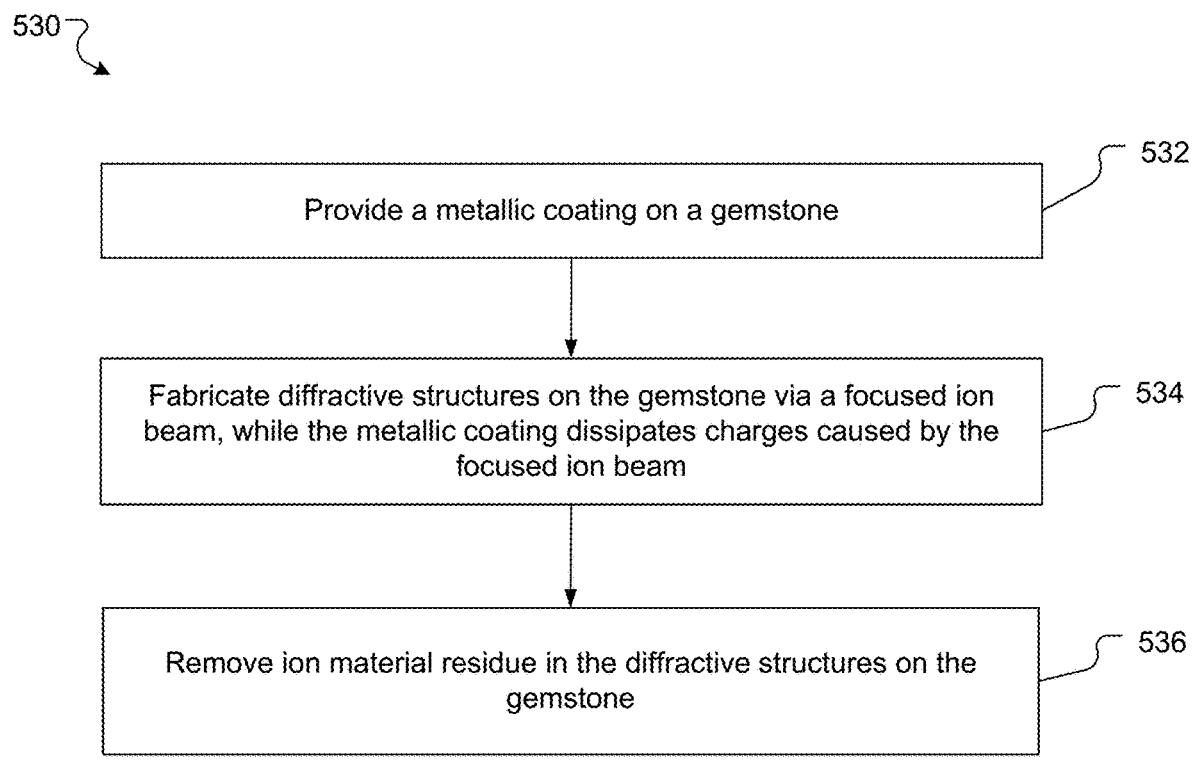
FIG. 5B is a flowchart of an example process of fabricating diffractive structure on a gemstone.

FIG. 5B is a flowchart of an example process 530 of fabricating diffractive structures on a gemstone. The process 530 can be applied in step 510 of the process 500.

A metallic coating is provided on the gemstone to be fabricated with diffractive structures (532). The gemstone can be positioned in a chamber and the metallic coating can be deposited onto an outer surface of the gemstone. The outer surface includes multiple facets selected to be fabricated with the diffractive structure. In some cases, the metallic coating includes gold. In some cases, the metallic coating includes gold palladium.

Diffractive structures are fabricated on the gemstone, e.g., on HOV regions of the selected facets, via a focused ion beam (534). The fabrication can be performed by a FIB machine. The FIB machine can include scanning electron microscope (SEM). Ions from an ion source, e.g., a gallium ion source, can be accelerated and focused onto the HOV regions on the selected facets. Ions in the focused ion beam can be used to remove material of the gemstone to form the diffractive structure. The metallic coating is configured to prevent (or eliminate) charging by the flow of positively charged ions during the FIB fabrication process. A thickness of the metallic coating is controlled such that the metallic coating is thick enough to dissipate charges caused by the focused ion beam and is thin enough for the focused ion beam to go through to reach the HOV regions. The remaining metallic coating can be removed, e.g., before or after step 536.

Some of ion material (e.g., gallium) in the focused ion beam can be impregnated into the facets during the fabrication process and remain in the diffractive structures (or on surfaces of the diffractive structures) after the fabrication process. The ion material residue may render the diffractive structures visible to a human eye, with or without a jeweler's loupe.

The ion material residue in the diffractive structures on the gemstone is removed (536). In some implementations, substantially all of the ion material residue visible to the human eye, or with the jeweler's loupe, can be removed. Thus, the diffractive structures on the gemstone can be invisible to the human eye, or with the jeweler's loupe. The loupe can have a magnification of no less than 5×, 10×, 15×, 20×, 25×, or 30×. The diffractive structures can be invisible under a microscope such as a Gemolite of Gemological Institute of America (GIA). The ion material residue can be removed by heating, cleaning or any other suitable methods.

Figure 5C:
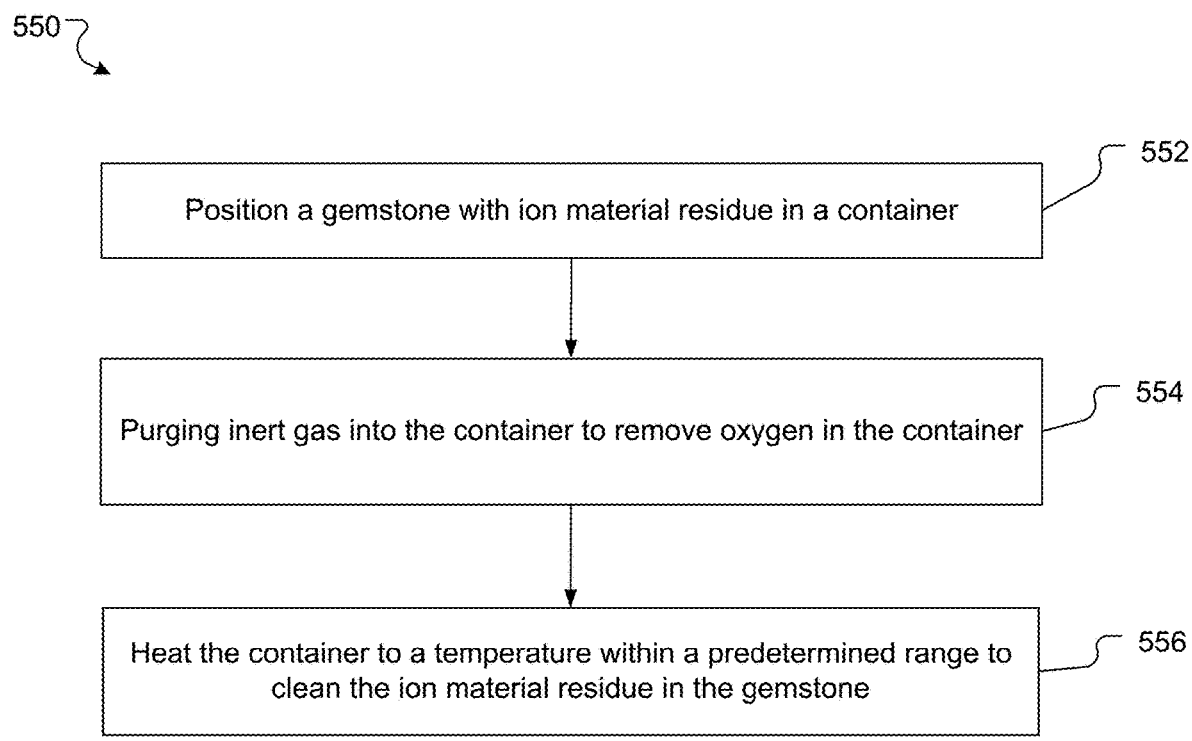
FIG. 5C is a flowchart of an example process of removing ion beam residue on a gemstone.

FIG. 5C is a flowchart of an example process 550 of removing ion beam residue on a gemstone by heating. The process 550 can be applied in step 536 of the process 530.

The gemstone with ion material residue is positioned in a container (552). The gemstone can be the gemstone fabricated with diffractive structures according to step 500 and/or step 530. The container can be an oven. The ion material residue can include gallium or a composite of gallium such as oxidized gallium.

Before heating the container, inert gas is purged into the container to remove oxygen in the container (554). The amount of oxygen in the container can be substantially reduced such that the ion material residue is not oxidized by the oxygen during heating and the gemstone material can be prevented from oxidizing. The inert gas can be nitrogen or any other suitable gases.

After removing the oxygen in the container, the container is heated to a temperature within a predetermined range to clean the ion material residue in the gemstone, e.g., by melting and/or evaporating the ion material residue (556). The predetermined range can be a range between 1100 degrees to 1200 degrees Fahrenheit. The container is heated no higher than 1300 degrees Fahrenheit while the gemstone is positioned in the container. In some cases, heating the container to clean the ion material residue can include heating the container at a temperature for a time period (or a dwell time) determined based on one or more characteristics of the gemstone and/or one or more characteristics of the ion material residue. The one or more characteristics of the gemstone can include a weight of the gemstone. When a gemstone has a larger size or something abnormal with the gemstone and/or the ion material residue, the time period can be longer. For example, for gemstones having a weight no more than 1.25 cwt (carat total weight), the time period at a heating temperature, e.g., within the temperature range of 1100-1200 degrees Fahrenheit, can be 10 to 20 minutes. If a gemstone has a weight more than 2.5 cwt, the dwell time can more than 25 minutes (or 30 minutes). The heating temperature and the dwell time period can be optimized to achieve effective manufacturing (e.g., with low cost and high throughput).

In some examples, cleaning the ion material residue can include removing substantially all of the ion material residue visible at a magnification, e.g., 5×, 10×, 15×, 20×, 25×, or 30×. In some cases, after the cleaning, the ion material still remaining in the gemstone can not be considered as a flaw on the gemstone.

FIG. 6 is a flowchart of an example process 600 of determining a diffractive structure on a high optical value region of a gemstone. The process 600 can be used to determine the high optical value region on a surface of the gemstone and determine a corresponding diffractive structure for the high optical value region by performing optical simulation on a three-dimensional model of the gemstone. The gemstone can be used as a representative gemstone. The process 600 can be similar to the process 100 as described in a U.S. Provisional Patent Application Ser. No. 62/540, 844, entitled "MANAGING OPTICAL PERFORMANCE OF GEMSTONES WITH DIFFRACTIVE STRUCTURES" and filed on Aug. 3, 2017, whose content is hereby incorporated by reference in its entirety.

The process 600 includes two major steps: determining a diffractive structure for the gemstone (602) and fabricating the diffractive structure on the gemstone (610). The first major step 602 can be performed by a computing system including one or more processors. The second major step 610 can be performed by a fabrication machine and optionally in combination with the computing system. The process 600 can also optionally include a third step 616 to measure an optical performance of the gemstone after the diffractive structure is fabricated on the gemstone. Note that the fabrication step 610 and/or the performance measurement step 616 can be used in the process 300 of FIG. 3, the process 400 of FIG. 4, or the process 500 of FIG. 5.

A three-dimensional (3D) model of the gemstone is obtained (604). The 3D model of the gemstone can be obtained by scanning the gemstone in three dimensions, for example, by using a scanning machine such as a 3D scanner, a camera system, a dimension HD (high definition) system, or a Diascan S+ system. Information of the 3D model can be stored as a computer file, e.g., a STereoLithography file (*.STL). The 3D model can be read, viewed, and/or edited by the computing system. The 3D model of the gemstone includes representations of surfaces of the gemstone and optionally additional details such as surface defects and internal structures. In some cases, the 3D model of the gemstone is obtained by receiving a computer file from another system. The computer file includes information of the 3D model. The computer file can be generated when or after a raw gemstone is cut or polished to be the gemstone.

A high optical value region on a surface of the gemstone is identified by analyzing the three-dimensional model (606). The region can be identified by analyzing the 3D model using a light simulation algorithm to simulate light propagation through the 3D model, e.g., via optical paths of a number of light rays based on reflection, refraction, and diffraction. The light simulation algorithm can include a ray-tracing algorithm based on a geometric optical approximation of light propagation, a diffraction algorithm, a simulation of Maxwell's equations which can be performed using finite difference time-domain (FDTD) or finite element methods (FEM), or any combinations or modifications thereof. The simulation algorithm can be implemented in a software.

The identified region can have a higher optical value than one or more other regions on the surface, where the identified region has a size substantially the same as each of the other regions on the surface. The optical value can be defined as light contribution of the region on the surface to an overall appearance of the gemstone. The optical value can be considered as an optical impact value used to evaluate the light reflection contributed by the region. In some cases, analyzing the 3D model of the diamond includes simulating propagation of an incident light through the gemstone and reflected by the surface and generating an irradiance plot representing light reflection distribution of the light on the surface. That is, if there is more light hitting and being reflected by a region of the surface, there can be more energy enclosed in the region of the surface in the irradiance plot. The propagation of the light can be from a virtual light source to a virtual camera via one or more optical paths in the gemstone and internally reflected by the surface. The optical value can be defined as a ratio of an energy disclosed in the region and a total energy enclosed in the surface. The identified region can have the highest ratio among the regions on the surface that have a substantially same size. A maximum irradiance on the surface can be at a center of the region.

In some examples, the optical value of the identified region on the surface is compared to a predetermined threshold. If the optical value of the identified region is smaller than the predetermined threshold, it can be determined that the surface is not good. It can be further determined not to arrange a diffractive structure on the surface. If all the surfaces of the gemstone are determined to be not good, it can be determined not to arrange any diffractive structure on the gemstone. In contrast, if the optical value of the identified region is identical to or larger than the predetermined threshold, it can be determined that the surface is good. It can be further determined to arrange a diffractive structure on the surface.

The predetermined threshold can be determined based on one or more properties of the gemstone. For example, the identified region can have a predetermined size, and the predetermined threshold can be associated with the predetermined size. In a particular example, the predetermined size is about 30% of a total size of the surface, and the predetermined threshold is about 50%.

In some implementations, a total energy enclosed in the surface in the irradiance plot is determined and compared to a threshold. If the total energy is smaller than the threshold, it can be determined that the surface is not good. It can be further determined not to arrange a diffractive structure on the surface.

A diffractive structure is determined to be arranged on the identified region of the surface of the gemstone (608), such that the gemstone with the diffractive structure has a higher optical performance than without the diffractive structure. The diffractive structure is configured to cause beam steering, diffractive or dispersion effects, or any combination thereof. The diffractive structure can include a diffraction grating. The diffraction grating can be configured to diffract the incident light into a number of angularly separated diffractive orders. If the incident light is a white light, the white light can be diffracted or dispersed into a number of different colors. The diffraction grating can be configured to diffract the light into an output light with a special color, e.g., red, blue, green, violet, or any other suitable color, which is stronger than other colors in the output light if any. The diffraction grating can also be configured to diffract the light into an output light with two or more special colors that are stronger than other colors in the output light. Thus, by using the diffraction grating to control the light (e.g., either making particular light components dominant or be suppressed) in the gemstone, the gemstone can be customized to appear a particular color favorable to a customer. The diffraction grating can also be configured to have the beam steering capability. Given light incident from a particular direction, the diffraction grating is configured to direct as much of the incident light as possible to exit at specified angles. For example, when the gemstone is a round brilliant cut diamond including a crown and a table, the diffraction grating on a facet of the diamond is configured to direct as much as possible light out from the crown or the table of the diamond, such that the optical performance (or optical appearance) of the diamond with the diffraction grating can be enhanced. The beam steering capability of the diffraction grating can be controlled by adjusting one or more parameters of the diffraction grating, including a depth, a width or a width varying with distance, and an orientation.

Determining the diffractive structure can include determining one or more parameters of the diffractive structure. For a diffraction grating, the one or more parameters can include a period, a width, a depth, an orientation, a shape, and a blazed angle. In a particular example, the diffraction grating has a period in a range of about 1 nm to 10 microns. In a particular example, the diffraction grating has a depth in a range of about 1 nm to 1 micron. In a particular example, the diffraction grating has an orientation in a range of 0 degree to 90 degree. In a particular example, the diffraction grating has an orientation in a range of −90 degree to 0 degree. Note that "in a range" herein can also include lower and upper boundary values of the range. The diffraction grating can be a periodic structure, a quasi-periodic structure, or non-periodic structure. For example, a width of the diffraction grating can be varying with distance along a direction. The diffraction grating can be a uniform structure or non-uniform structure. For example, a depth of the diffraction grating can be varying with distance along a direction.

The diffractive structure can be determined by simulating propagation of an incident light from a virtual light source to a virtual camera through the gemstone and diffracted by the diffractive structure on the identified region of the surface via one or more optical paths. The diffracted light can exit from the gemstone from an output surface of the gemstone. For example, a crown and a table of a diamond can be the output surface. The simulation can be performed by the light simulation algorithm mentioned above or any other algorithm that can simulate the light propagation via reflection, refraction, and diffraction or dispersion. Data representing optical appearance of the diamond can be detected on the virtual camera.

When light enters a gemstone (e.g., a diamond), it travels through the gemstone and is reflected off or diffracted by interior surfaces (e.g., facets) of the gemstone. Then the light either leaves the diamond as a white light and/or the light divides into one or more spectral colors, e.g., red, orange, yellow, green, blue, and/or violet. The total intensity of the output light from the gemstone, including the white light and the spectral-colored light, is called brightness or brilliance. The colorfulness of the output light is called fire. A special color that is much stronger than any other colors in the output light is called color. As a viewer or the gemstone moves, an effect called scintillation occurs—visible as alternating flashes of white and spectral-colored light and the contrast of dark and light that moves around the gemstone. This contrast is dynamic and causes sparkle. The optical performance of the gemstone can include at least one of brilliance (or brightness), fire (or colorfulness), or scintillation (or sparkle).

In some cases, the optical performance includes brilliance (or brightness). The brilliance of the gemstone can be determined based on the generated data or the generated average brightness. Determining the diffractive structure can include determining the one or more parameters of the diffractive structure such that an average brightness of the optical appearance of the gemstone is larger than the gemstone without the diffractive structure. Determining the diffractive structure can also include adjusting the one or more parameters of the diffractive structure to maximize the brilliance of the gemstone, e.g., the average brightness of the gemstone.

In some cases, the optical performance includes fire (or colorfulness). The fire of the gemstone can be determined based on the generated data or the average color. Determining the diffractive structure can include determining the one or more parameters of the diffractive structure such that the optical appearance of the gemstone has more fire than the gemstone without the diffractive structure. Determining the diffractive structure can also include adjusting the one or more parameters of the diffractive structure to maximize the fire of the gemstone.

In some cases, the optical performance includes a special color. Determining the diffractive structures can include determining the one or more parameters of the diffractive structure such that the light exiting from the gemstone has the special color with the largest brightness than the other colors in the light, e.g., a dominant color. Determining the diffractive structure can also include adjusting the one or more parameters of the diffractive structure to maximize the brightness of the special color.

In some cases, the optical performance includes sparkle (or scintillation). The sparkle of the gemstone can be determined by moving the virtual light source or the virtual camera in relative to the gemstone and then determining a difference of the generated data before and after the moving. Determining the diffractive structure can include determining the one or more parameters of the diffractive structure such that the optical appearance of the gemstone has more sparkle than the gemstone without the diffractive structure. Determining the diffractive structure can also include adjusting the one or more parameters of the diffractive structure to maximize the sparkle of the gemstone.

In some implementations, the process 600 further includes determining a second diffractive structure for a second surface of the gemstone. Similar to step 606, a second region on the second surface of the gemstone is identified by analyzing the 3D model of the gemstone. The second region can have an optical value higher than one or more other regions on the second surface or higher than a predetermined threshold or both. The process 600 can further include determining the second diffractive structure to be arranged on the identified second region on the second surface, such that the gemstone with the diffractive structure for the surface and the second diffractive structure for the second surface has a higher optical performance than without the diffractive structures. In some cases, the second surface and the surface are adjacent. In some cases, the second surface is selected to be separated from the surface.

When a diffractive structure is arranged on a surface of the gemstone, on one side, the diffractive structure diffracts light into different directions, which may cause loss of light and reduce the brilliance of the gemstone; on the other side, the diffractive structure can perform beam steering on the light and direct the light as much as possible to a desired output surface. Moreover, when the diffractive structure is arranged on a first surface, the light can be diffracted to a second surface opposite to the first surface (or adjacent to the first surface) and reflected or bounced by the second surface, which can increase (e.g., double) the effect of the diffractive structure and also minimize the light loss. Thus, a number of factors can be considered for determining multiple diffractive structures on the gemstone, including the number of diffractive structures, the sizes of the diffractive structures, and the surfaces selected to be arranged with the diffractive structures.

In some examples, the gemstone includes a first surface and a second surface opposite to each other, e.g., in a planar view of the gemstone. If the first surface is selected to be arranged with a diffractive structure, it can be determined not to arrange a diffractive structure on the second surface.

In some implementations, the gemstone includes a number of pairs of surfaces. In a planar view of the 3D model of the gemstone, two surfaces of each pair are opposite to each other. One surface from each pair can be selected to be arranged with a diffractive structure, and the other surface from the same pair can be left blank without arranging a diffractive structure. In some cases, selecting one surface from each pair for the gemstone can include selecting the surfaces from the number of pairs such that light reflection by the surfaces is balanced (e.g., evenly distributed or uniform) in the gemstone, or such that the selected surfaces are evenly distributed in the gemstone. For example, the gemstone has 4 pairs, including surfaces 1 and 5, surfaces 2 and 6, surfaces 3 and 7, and surfaces 4 and 8. The selected surfaces to be arranged with diffractive structures are surfaces 1, 3, 6, and 8. In such a way, less number of diffractive structures can be determined and fabricated on the gemstone, which can reduce cost and/or improve the optical performance of the gemstone.

After determining one or more diffractive structures on one or more surfaces of the gemstone, the process 600 proceeds to the second major step 610, that is, to fabricate the determined diffractive structures on the gemstone by the fabrication machine. The fabrication machine can include a focused-ion-beam (FIB) machine, a micro- or nano-patterning machine such as micro- or nano-lithography system, or any suitable machine or system.

In some implementations, the diffractive structures can be deposited onto the surfaces of the gemstone. In some implementations, the diffractive structures can be patterned (or etched) into or on the gemstone surface itself. The diffractive structures can be located within the gemstone.

The gemstone is aligned with respect to the fabrication machine based on the 3D model of the gemstone (612), such that the fabrication machine can fabricate the determined diffractive structure on the identified region of the surface of the gemstone. The gemstone can be digitally photographed. The digital photographs can be processed, e.g., by the computing system, to determine an orientation of the gemstone and further to match or map the orientation of the gemstone with the 3D solid model or other means and the identified region on the surface of the gemstone. The gemstone can be placed into the fabrication machine, e.g., into a chamber of the fabrication machine. The matching or mapping information can be fed into the fabrication machine. The gemstone can be aligned, e.g., by using a movable stage with an XYZ, rotation, and azimuth motion, such that the identified region on the surface is matched to where the fabrication machine writes a pattern of the diffractive structure.

The determined diffractive structure is fabricated on the identified region of the surface of the gemstone based on the alignment (614). The fabrication machine can receive information of the diffractive structure from the computing system, and fabricate the diffractive structure on the identified region of the surface of the gemstone based on the received information and the alignment.

In some implementations, after fabricating a diffractive structure on a surface of the gemstone, the gemstone can be aligned with respect to the fabrication machine such that a second identified region on a second surface of the gemstone is matched to where the fabrication machine writes a corresponding second diffractive structure. Then, the fabrication machine fabricates the corresponding second diffractive structure on the second identified region on the second surface of the gemstone. The fabrication machine can perform a loop to fabricate multiple diffractive structures on multiple different surfaces on the gemstone. The fabrication machine can also continue another loop to fabricate diffractive structures on another gemstone.

In some implementations, after fabricating a diffractive structure on a surface of the gemstone (614), an optical performance of the gemstone with the fabricated diffractive structure is measured (616). The measurement can be performed by an operator using an optical device or system such as a microscope system. In some cases, based on a result of the measurement, one or more properties of the diffractive structure can be adjusted to adjust (or optimize) the optical performance of the gemstone. For example, the result of the measurement can be input into a computing system and the computing system can perform step 608 to adjust the one or more properties of the diffractive structure. The diffractive structure with the adjusted properties can be fabricated on another surface on the same gemstone or on a surface of another gemstone. In some cases, based on a result of the measurement, another diffractive structure to be arranged on a second surface of the gemstone can be re-determined or adjusted.

In some implementations, two or more diffractive structures are determined to be arranged on two or more corresponding surfaces of the gemstone. After the two or more diffractive structures are fabricated on the surfaces of the gemstone, the gemstone with the fabricated diffractive structures is measured to determine its optical performance. Based on the result of the measured optical performance, one or more properties of the diffractive structures can be adjusted or different surfaces may be selected to be arranged with diffractive structures on a gemstone.

In some implementations, different gemstones are fabricated with different diffractive structures, such that the gemstones are identifiable from each other based on the corresponding diffractive structures fabricated on them. In some cases, diffractive structures for different gemstones can be made different during the simulation, e.g., at step 608. In some cases, diffractive structures for different gemstones can be made different during the fabrication, e.g., at step 614. The fabrication machine can be controlled to modify one or more parameters of a diffractive structure to be fabricated on different gemstones.

While this disclosure contains many specific implementation details, these should not be construed as limitations on the scope of any invention or on the scope of what may be claimed, but rather as descriptions of features that may be specific to particular implementations of particular inventions. Certain features that are described in this disclosure in the context of separate implementations can also be implemented in combination in a single implementation. Conversely, various features that are described in the context of a single implementation can also be implemented in multiple implementations separately or in any suitable sub-combination. Moreover, although features may be described as acting in certain combinations and even initially claimed as such, one or more features from a claimed combination can in some cases be excised from the combination, and the claimed combination may be directed to a sub-combination or variation of a sub-combination.

Particular implementations of the subject matter have been described. Other implementations, alterations, and permutations of the described implementations are within the scope of the following claims as will be apparent to those skilled in the art. While operations are depicted in the drawings or claims in a particular order, this should not be understood as requiring that such operations be performed in the particular order shown or in sequential order, or that all illustrated operations be performed (some operations may be considered optional), to achieve desirable results.

Accordingly, the earlier provided description of example implementations does not define or constrain this disclosure. Other changes, substitutions, and alterations are also possible without departing from the spirit and scope of this disclosure. Accordingly, other embodiments are within the scope of the following claims.

What is claimed is:

1. A method of improving optical performance of a gemstone comprising:
   obtaining a plurality of gemstone characteristics of a gemstone;
   determining that the gemstone exhibits each of the plurality of gemstone characteristics within a respective predetermined range; and
   identifying, for the gemstone, a diffractive structure setting associated with a combination of the respective predetermined ranges for the plurality of gemstone characteristics;
   wherein the plurality of gemstone characteristics comprises at least a first gemstone characteristic and a second gemstone characteristic, and
   wherein determining that the gemstone exhibits each of the plurality of gemstone characteristics within a respective predetermined range comprises: determining that the gemstone exhibits the first gemstone characteristic within a first predetermined range and a second gemstone characteristic within a second predetermined range.

2. The method of claim 1, wherein the plurality of gemstone characteristics of the gemstone is obtained based on at least one of:
   geometrical cut parameters of the gemstone,
   a three-dimensional model of the gemstone, or
   geometrical measurement of an outer surface of the gemstone.

3. The method of claim 1, wherein the diffractive structure setting and the combination are stored and associated in a repository that stores and associates respective diffractive structure settings with different combinations of ranges of gemstone characteristics.

4. The method of claim 1, wherein the gemstone is a diamond having a culet, a pavilion, a girdle, a crown, and a table, and
   wherein the plurality of gemstone characteristics comprises one or more of a crown percentage, a table percentage, a depth proportion, a joint angle between a crown and a pavilion, and symmetry.

5. The method of claim 1, wherein the diffractive structure setting comprises:
information of a plurality of facets of a gemstone to be fabricated with diffractive structures,
information of a respective high-optical-value (HOV) region on each of the plurality of facets, and
information of a respective diffractive structure to be fabricated in the respective HOV region on each of the plurality of facets.

6. The method of claim 5, wherein the plurality of facets is selected from a total number of facets of the gemstone, and
wherein the selected facets are not opposite to each other.

7. The method of claim 5, wherein the information of the respective diffractive structure comprises:
one or more of parameters of the respective diffractive structure including a depth, a pitch, uniformity, a shape, an angle, and a number of cuts.

8. The method of claim 5, wherein the information of the respective high-optical-value (HOV) region on each of the plurality of facets comprises:
a relative location of the respective HOV region on the facet,
a shape of the respective HOV region, and
a relative size of the respective HOV region to the facet.

9. The method of claim 1, further comprising:
fabricating diffractive structures on the gemstone according to the diffractive structure setting.

10. The method of claim 9, wherein fabricating the diffractive structures on the gemstone comprises:
milling the diffractive structures on the facets of the gemstone by using a focused ion beam; and
removing ion material residue in the fabricated diffractive structures.

11. The method of claim 10, wherein removing the ion material residue in the fabricated diffractive structures comprises:
heating the gemstone with the fabricated diffractive structures in a container to reduce an amount of the ion material residue in the gemstone.

12. The method of claim 11, further comprising:
before the heating, purging the container with inert gas to reduce an amount of oxygen in the container.

13. The method of claim 11, wherein the container is an oven and is heated to a temperature between 1100-1200 degrees Fahrenheit and the ion material residue is melted at the temperature.

14. The method of claim 11, wherein heating the gemstone with the fabricated diffractive structure comprises:
heating the container at a temperature for a time period determined based on one or more characteristics of the gemstone including a weight.

15. The method of claim 10, further comprising:
before the milling, depositing a metallic coating on the gemstone,
wherein a thickness of the metallic coating is controlled such that the metallic coating is thick enough to dissipate charges caused by the focused ion beam and is thin enough for the focused ion beam to go through.

16. The method of claim 15, wherein the metallic coating comprises one of gold and gold palladium.

17. A method of improving optical performance of gemstones comprising:
identifying a plurality of gemstone characteristics of gemstones, wherein the plurality of gemstone characteristics comprise at least a first gemstone characteristic and a second gemstone characteristic;
determining that the gemstones exhibit each of the plurality of gemstone characteristics within a respective predetermined range;
identifying, for the gemstones, a diffractive structure setting associated with a combination of the respective predetermined ranges for the plurality of gemstone characteristics;
wherein determining that the gemstones exhibit each of the plurality of gemstone characteristics within a respective predetermined range comprises:
determining that a first plurality of gemstones each exhibit a first combination of the first gemstone characteristic within a first range and a second gemstone characteristic within a second range; and
determining that a second plurality of gemstones each exhibit a second combination of the first gemstone characteristic within a third range and the second gemstone characteristic within a fourth range,
wherein the second combination is different from the first combination;
fabricating diffractive structures in the first plurality of gemstones according to a first diffractive structure setting; and
fabricating diffractive structures in the second plurality of gemstones according to a second diffractive structure setting that is different than the first diffractive structure setting.

18. A method of improving optical performance of a gemstone comprising:
obtaining a plurality of gemstone characteristics of a gemstone;
determining that the gemstone exhibits each of the plurality of gemstone characteristics within a respective predetermined range; and
identifying, for the gemstone, a diffractive structure setting associated with a combination of the respective predetermined ranges for the plurality of gemstone characteristics;
fabricating diffractive structures on the gemstone according to the diffractive structure setting, wherein fabricating the diffractive structures on the gemstone comprises:
depositing a metallic coating on the gemstone;
milling the diffractive structures on the facets of the gemstone having the metallic coating by using a focused ion beam; and
removing ion material residue in the fabricated diffractive structures;
wherein a thickness of the metallic coating is controlled such that the metallic coating is thick enough to dissipate charges caused by the focused ion beam and is thin enough for the focused ion beam to go through.

19. The method of claim 18, wherein the metallic coating comprises one of gold and gold palladium.

* * * * *